(12) United States Patent
LaPorte et al.

(10) Patent No.: US 10,744,215 B2
(45) Date of Patent: Aug. 18, 2020

(54) SYSTEMS AND METHODS FOR SANITIZING PORTABLE DEVICES

(71) Applicant: Phonesoap LLC, Orem, UT (US)

(72) Inventors: Wesley LaPorte, Provo, UT (US); Daniel Barnes, Orem, UT (US)

(73) Assignee: Phonesoap LLC, Lehi, UT (US)

(*) Notice: Subject to any disclaimer, the term of this patent is extended or adjusted under 35 U.S.C. 154(b) by 0 days.

(21) Appl. No.: 16/571,062

(22) Filed: Sep. 14, 2019

(65) Prior Publication Data

US 2020/0013502 A1 Jan. 9, 2020

Related U.S. Application Data

(63) Continuation of application No. 15/681,337, filed on Aug. 18, 2017.

(Continued)

(51) Int. Cl.
*A61L 2/08* (2006.01)
*G08B 21/24* (2006.01)
(Continued)

(52) U.S. Cl.
CPC .......... *A61L 2/08* (2013.01); *A61L 2/10* (2013.01); *A61L 2/24* (2013.01); *G08B 21/245* (2013.01); *G16H 40/40* (2018.01); *A61L 2202/11* (2013.01); *A61L 2202/122* (2013.01); *A61L 2202/14* (2013.01); *G16H 40/20* (2018.01); *G16H 40/67* (2018.01)

(58) Field of Classification Search
CPC ........... A61L 2/08; A61L 2/10; A61L 2202/14
See application file for complete search history.

(56) References Cited

U.S. PATENT DOCUMENTS

| 6,656,424 B1 | 12/2003 | Deal |
| 6,911,177 B2 | 6/2005 | Deal |

(Continued)

FOREIGN PATENT DOCUMENTS

| CN | 101951004 | 1/2011 |
| KR | 2003033475 | 5/2003 |

(Continued)

OTHER PUBLICATIONS

International Search Report and Written Opinion dated Oct. 18, 2018 for international application PCT/US2018/037210.

(Continued)

*Primary Examiner* — Eliza W Osenbaugh-Stewart
(74) *Attorney, Agent, or Firm* — Stoel Rives LLP

(57) ABSTRACT

A sanitization device comprises an enclosure comprising emitters configured to emit sanitizing electro-optical radiation into an interior compartment. The sanitization device further includes a panel having an open configuration and a closed configuration adapted to enclose the inner compartment. The panel includes an inner surface forming a depression configured to receive a portable device when the panel is in the open configuration and to secure the portable device as the panel transitions to the closed configuration. The sanitization device may further comprise an actuator configured to transition the panel between the open and closed configurations in response to inputs received via a touchless input interface.

23 Claims, 10 Drawing Sheets

Related U.S. Application Data

(60) Provisional application No. 62/519,126, filed on Jun. 13, 2017.

(51) Int. Cl.
    *G16H 40/40*     (2018.01)
    *A61L 2/10*     (2006.01)
    *A61L 2/24*     (2006.01)
    *G16H 40/67*     (2018.01)
    *G16H 40/20*     (2018.01)

(56) References Cited

U.S. PATENT DOCUMENTS

| | | |
|---|---|---|
| 7,175,806 B2 | 2/2007 | Deal et al. |
| 7,424,314 B2 | 9/2008 | Park |
| 7,829,016 B2 | 11/2010 | Deal et al. |
| 8,067,750 B2 | 11/2011 | Deal |
| 8,203,124 B2 | 6/2012 | Havens et al. |
| 8,256,568 B2 | 9/2012 | Lin |
| 8,296,493 B1 * | 10/2012 | Engelhardt ............... A61L 2/20 710/303 |
| 8,522,917 B1 | 9/2013 | Oh et al. |
| 8,816,301 B2 | 8/2014 | Stibich et al. |
| 2002/0009195 A1 | 1/2002 | Schon |
| 2005/0023483 A1 | 2/2005 | Fenc |
| 2006/0188389 A1 | 8/2006 | Levy |
| 2008/0175761 A1 | 7/2008 | Thur et al. |
| 2009/0191100 A1 | 7/2009 | Deal |
| 2010/0044582 A1 | 2/2010 | Cooper et al. |
| 2010/0096963 A1 | 4/2010 | McLaughlin et al. |
| 2010/0124040 A1 | 5/2010 | Diebel et al. |
| 2010/0219012 A1 | 9/2010 | Baumbach |
| 2011/0110819 A1 | 5/2011 | Allen et al. |
| 2012/0313014 A1 | 12/2012 | Stibich et al. |
| 2012/0313532 A1 | 12/2012 | Stibich et al. |
| 2013/0063922 A1 * | 3/2013 | La Porte ............... A61L 2/10 361/807 |
| 2013/0224086 A1 | 8/2013 | Stibich et al. |
| 2013/0330235 A1 | 12/2013 | Stibich et al. |
| 2014/0183377 A1 | 7/2014 | Bettles et al. |
| 2014/0301893 A1 * | 10/2014 | Stroup ............... A61L 2/10 422/24 |
| 2016/0158395 A1 | 6/2016 | Hughes et al. |
| 2017/0296299 A1 * | 10/2017 | Yun ............... A61C 19/002 |
| 2018/0357385 A1 | 12/2018 | LaPorte et al. |

FOREIGN PATENT DOCUMENTS

| | | |
|---|---|---|
| KR | 2006012144 | 2/2006 |
| KR | 100675770 | 1/2007 |
| KR | 100956373 | 5/2010 |
| KR | 2011024651 | 3/2011 |
| WO | 2006022466 | 3/2006 |
| WO | 2006075894 | 7/2006 |
| WO | 2018231903 | 12/2018 |

OTHER PUBLICATIONS

LaPorte, et al., Notice of Allowance dated Feb. 3, 2016 for U.S. Appl. No. 14/216,755.

LaPorte, et al., Notice of Allowance dated Oct. 17, 2014 for U.S. Appl. No. 13/615,115.

LaPorte, et al., Notice of Allowance dated Sep. 10, 2015 for U.S. Appl. No. 14/216,755.

LaPorte, et al., Office Action dated Aug. 19, 2014 for U.S. Appl. No. 14/216,755.

LaPorte, et al., Office Action dated Mar. 10, 2015 for U.S. Appl. No. 14/216,755.

LaPorte, et al., Office Action dated May 2, 2014 for U.S. Appl. No. 13/615,115.

* cited by examiner

SYSTEMS AND METHODS FOR SANITIZING PORTABLE DEVICES

CROSS-REFERENCES TO RELATED APPLICATIONS

The Application Data Sheet filed herewith is incorporated by reference. This application claims priority to U.S. patent application Ser. No. 15/681,337, filed Aug. 18, 2017, which claims priority to U.S. Provisional Patent Application No. 62/519,126, filed Jun. 13, 2017, each of which is hereby incorporated by reference.

TECHNICAL FIELD

The disclosure relates to systems and methods for managing device sanitization and, more specifically, to systematically sanitizing a plurality of managed electronic devices using electro-optical radiation.

BRIEF DESCRIPTION OF THE DRAWINGS

This disclosure includes and references the accompanying drawings, which provide a more particular description of the embodiments disclosed herein. The disclosure, however, is not limited to the particular embodiments depicted in the figures. The teachings of the disclosure may be utilized and/or adapted to other embodiments, and/or changes may be made to the disclosed embodiments, without departing from the scope of the disclosure.

DETAILED DESCRIPTION

Figure 1:
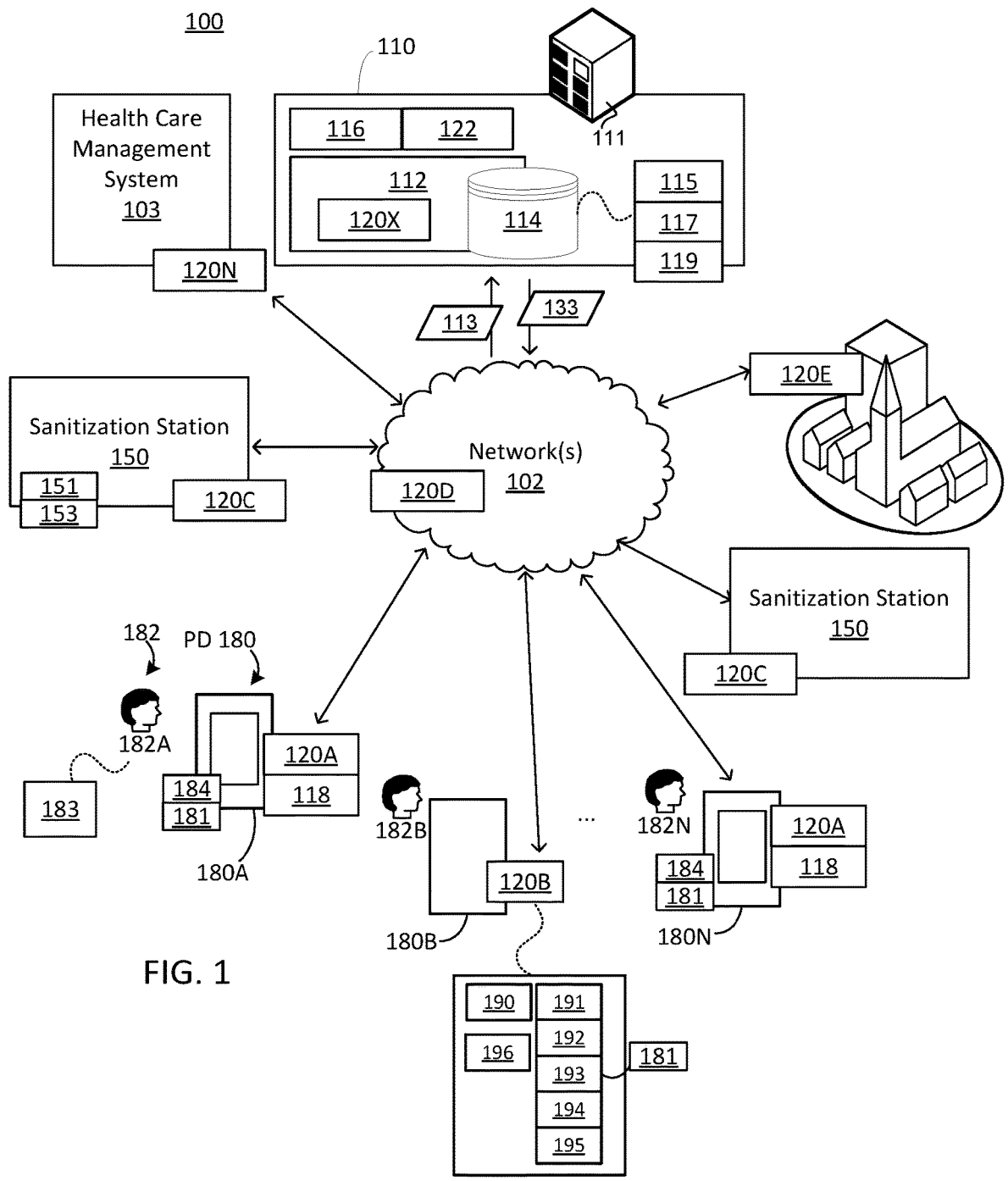
FIG. 1 is a schematic block diagram of one embodiment of a sanitization management system.

Industries commonly rely on portable devices (PDs), such as portable electronic devices, to perform tasks, gather and access information, enter and update information, and/or the like. PDs allow members of an organization the freedom to move about while maintaining connectivity. For example, a health care professional may use PDs to, inter alia, examine patients, treat patients, enter patient information, access patient records, update patient records, record examination results, record treatment results, record patient diagnoses, perform research, submit prescriptions, and so on. The surfaces of a PD may, however, become contaminated during use. A PD may become contaminated with harmful materials, such as toxic materials, radioactive materials, poisons, allergens, and/or the like. PDs may also become contaminated with potentially harmful organisms, such as microbes, pathogens, viruses, bacteria, and/or the like. Device contamination is especially problematic when PDs are used for health care-related tasks (e.g., used in a doctor's office, a hospital, or another care facility where the PDs are likely to be exposed to harmful organisms). Therefore, what is needed are systems, methods, and apparatus for managing device sanitization and, in particular, for systematically managing sanitization of PDs within an organization.

Disclosed herein are embodiments of an apparatus for sanitizing a portable electronic device, comprising: an enclosure comprising an interior compartment configured to receive a portable electronic device; a front panel to provide access to the interior compartment, the front panel comprising an interior surface that is transparent to ultraviolet radiation; and a hinge coupling the front panel to a bottom wall of the enclosure, the front panel to rotate relative to the enclosure about a fixed axis of rotation of the hinge, the front panel selectively rotating between an opened and a closed position. When the front panel is in the closed position, the interior surface of the front panel may be configured to secure the portable electronic device in a raised position, and when the front panel is in the opened position, the interior surface of the front panel may be configured to support the portable electronic device in a reclined position. The apparatus may further comprise one or more emitters configured to emit electro-optical radiation into the interior compartment, wherein at least one emitter is configured to emit electro-optical radiation into the interior compartment through the interior surface of the front panel. The front panel may be configured to stabilize the portable electronic device while rotating between an opened and a closed position. The front panel may further comprise a guide structure that does not interfere with ultraviolet radiation to stabilize the portable electronic device. The front panel may include a slot, grooves, and/or a high-friction surface configured to stabilize the portable electronic device. In the raised position, the portable electronic device may be positioned at an angle relative to the bottom wall of the enclosure, such that the front panel supports the portable electronic device in the raised position. The enclosure may be configured to be mounted on a wall.

Another embodiment of an apparatus for sanitizing a portable electronic device may comprise: an enclosure comprising an interior compartment configured to receive a portable electronic device; one or more emitters configured to emit electro-optical radiation into the interior compartment; a support configured to maintain the plurality of portable electronic devices such that substantially an entire surface of each of the plurality of portable electronic devices is exposed to electro-optical radiation emitted by the one or more emitters; an interface to receive touchless input from a user; and an actuator to open the enclosure in response to a touchless user input. The support may comprise a front panel to provide access to the interior compartment, the front panel comprising an interior surface that is transparent to ultraviolet radiation. The apparatus may further include a hinge coupling the front panel to a bottom wall of the enclosure, the front panel to rotate relative to the enclosure about a fixed axis of rotation of the hinge, the front panel selectively rotating between an opened and a closed position. The interface may comprise a sensor to detect external movement, and the actuator may be configured to open the enclosure when the sensor detects a predefined motion and/or motion in a particular external location. The actuator may be configured to open the enclosure in response to a user command entered on the portable electronic device.

Disclosed herein are embodiments of a system for sanitizing a plurality of portable electronic devices, comprising: a sanitizing station; and a server in communication with the plurality of portable electronic devices and the sanitizing station. The sanitizing station may include an enclosure comprising an interior compartment configured to receive at least one of a plurality portable electronic devices, and one or more emitters configured to emit electro-optical radiation into the interior compartment. The server may comprise a processor and a non-transitory computer-readable medium with instructions stored thereon that, when executed by the processor, cause the server to perform operations to alert a user of a need to sanitize one of the plurality of portable electronic devices, the operations comprising: monitoring one or more conditions of each of the plurality of portable electronic devices, determining, based on the one or more one or more conditions, that a first portable electronic device requires sanitization according to one or more sanitizing rules, and instructing the user to perform a sanitization operation by use of the sanitization station. The sanitizing station may comprise a device detector to identify a portable electronic device being sanitized thereby. The sanitizing station may further include a transmitter to send a signal to identify the portable electronic device being sanitized thereby. The server may be configured to log and/or audit sanitization operations performed on respective portable electronic devices. The server may be further configured to log and/or audit sanitization policy violations pertaining to the portable electronic devices in accordance with one or more sanitizing rules. The monitored conditions may include, but are not limited to: a time since a last sanitization was performed on respective portable electronic devices; patient symptoms input, accessed, updated, researched, and/ or recorded on respective portable electronic devices; patients in the vicinity of respective portable electronic devices; location(s) of respective portable electronic devices; and so on. Instructing the user may comprise sending a signal to the first electronic device, the signal configured to cause the first portable electronic device to alert the user of a sanitization requirement (e.g., by displaying the alert, emitting a sound, locking the device, and/or the like).

FIG. 1 is a schematic block diagram of one embodiment of a sanitization management system 100. The sanitization management system 100 may comprise a sanitization manager 110 and one or more sanitization stations 150. The disclosed sanitization management system 100 may be configured to manage sanitization of one or more portable PDs 180 (e.g., PD 180A-N as illustrated in FIG. 1). The sanitization manager 110, sanitization station(s) 150, and PD 180 may be communicatively coupled via one or more communication networks 102. The sanitization manager 110 may be configured to implement, audit, and/or enforce a sanitization policy pertaining to the respective PD 180, which may comprise: a) registering the PDs 180 with the sanitization manager 110, b) monitoring the PDs 180, and c) ensuring that the registered PDs 180 conform to a particular sanitization policy (based on the monitoring of the PDs 180). The sanitization manager 110 may comprise a sanitization management server 111 and non-transitory data store 114. The sanitization management server 111 may comprise and/or be embodied by a computing device, comprising processing components, memory components, non-transitory storage components, human-machine interface (HMI) components, communication interface components, and/or the like (not shown in FIG. 1 to avoid obscuring the details of the illustrated embodiments). The processing components may include, but are not limited to: a circuit, a chip, a package, a microprocessor, a microcontroller, a central processing unit, a general-purpose processing unit, a special-purpose processing unit, processing circuitry, logic circuitry, an integrated circuit (IC), a System on a Chip (SoC), a Programmable System on a Chip (PsoC), a System in Package (SiP), an Application-specific Integrated Circuit (ASIC), configurable circuitry, programmable circuitry, a Field Programmable Gate Array (FPGA), a Complex Programmable Logic Device (CPLD), a Programmable Logic Array (PLA), and/or the like. The memory components may include, but are not limited to: cache memory, volatile memory, Random-Access Memory (RAM), Dynamic RAM (DRAM), Static RAM (SRAM), Thyristor RAM (TRAM), Zero-capacitor RAM (ZRAM), and/or the like. The non-transitory storage components may include, but are not limited to: a non-transitory storage device, a non-transitory memory device, a solid-state memory, a hard drive, a magnetic disk storage device, an optical storage device, a tape storage device, a Flash memory, a NAND-type Flash memory, a NOR-type Flash memory, a Programmable Metallization Cell (PMC) memory, a Silicon-Oxide-Nitride-Oxide-Silicon (SONOS) memory, a Resistive RAM (RRAM) memory, a Floating Junction Gate RAM (FJG RAM), a ferroelectric memory (FeRAM), a magnetoresistive memory (MRAM), a phase change memory (PRAM), an Electrically Erasable Programmable Read-Only Memory (EEPROM), a cache storage device, a remote storage device, a Network Attached Storage (NAS) device, and/or the like. The HMI components may include, but are not limited to: input/output devices, such as keyboards, pointer and/or gesture devices (e.g., mouse, touch pad, touch display, and/or the like), cameras, display devices, monitors, audio capture devices, audio output devices, haptic feedback devices, and/or the like. The network interface components may include, but are not limited to: network interface devices, network interface ports, network interface cards, network interface ports, communication buses, communication drivers, and/or the like.

As disclosed above, the sanitization manager 110 may receive monitoring metadata 113 pertaining to the respective PD 180 via the network(s) 102 (by use of a monitor 112). The monitoring metadata 113 may be maintained within, inter alia, the non-transitory data store 114. The sanitization manager 110 may use the monitoring metadata 113 to manage sanitization of the respective PD 180, which may comprise a) determining a "state" of the respective PD 180 (e.g., sanitization status of the PD 180), b) evaluating a sanitization policy 119 based on the determined state, and c)

generating corresponding sanitization management data 133 for the PD 180 configured to, inter alia, ensure that the PD 180 complies with the sanitization policy 119. As disclosed in further detail herein, the "state" of a PD 180 may correspond to, inter alia, a last sanitization operation performed on the PD 180, a time elapsed since the last sanitization operation, usage of the PD 180 since the last sanitization operation, location(s) of the PD 180 since the last sanitization operation, explicit sanitization requests (e.g., requests to require sanitization of the PD 180), and so on. The sanitization manager 110 may comprise a sanitization policy manager 116, which may be configured to analyze the monitoring metadata 113 of a PD 180 to determine, inter alia, the state of the PD 180, and determine a sanitization schedule for the PD 180 based on a sanitization policy 119 (and determined state).

The sanitization manager 110 may be further configured to initiate sanitization operations on the PDs 180 based on the determined state of the PDs 180 and/or the sanitization policy 119. The sanitization manager 110 may initiate a sanitization operation on a PD 180 using any suitable mechanism, including, but not limited to: issuing a sanitization message to the PD 180 via the network 102, issuing a sanitization directive to the PD 180 via the network 102, sending a sanitization schedule to the PD 180, forcing the PD 180 to implement a sanitization operation (e.g., by locking the PD 180), and/or the like.

In some embodiments, the sanitization manager 110 may comprise a management client 118. The management client 118 may be configured to operate on a "smart" PD 180. As used herein a "smart" PD 180 refers to a PD 180 that is capable of running and/or hosting one or more applications (e.g., the PD 180A and 180N of FIG. 1). A smart PD 180 may comprise a portable computing device, which may comprise processing components, memory components, non-transitory storage components, network interface components, HMI components, and/or the like, as disclosed herein. The management client 118 may be embodied as and/or comprise one or more of: an application, a user-level application, a kernel-level application, a driver, firmware, a boot image, and/or the like. In some embodiments, the management client 118 may be hosted on the sanitization management server 111 and/or be delivered to the PD 180 by the sanitization manager 110. The sanitization manager 110 and/or management client 118 may comprise one or more security measures to ensure the integrity of the management client 118 and/or prevent the management client 118 from being disabled. Such security measures may include, but are not limited to: embedding the management client 118 with the operating system, kernel, boot image, and/or firmware of the PD 180; implementing the management client 118 as a protected component (e.g., a kernel-level application, driver, or the like); maintaining a code signature for the management client 118; authenticating instructions comprising the management client 118; implementing a secure, cryptographic challenge-response protocol with the management client 118; and/or the like.

The management client 118 may be configured to receive and/or display information pertaining to the sanitization state of the PD 180 and/or sanitization policy 119 pertaining to the PD 180. Such information may include, but is not limited to: a sanitization schedule for the PD 180 (e.g., a time until a next sanitization operation should be performed), a sanitization time limit (e.g., a time by which a next sanitization operation must be performed on the PD 180), a sanitization command or directive (e.g., a notification requiring immediate sanitization of the PD 180), and/or the like. The management client 118 may be configured to display certain sanitization messages interstitially and/or modally, such that the display of the sanitization messages interrupts operation of the PD 180. A user 182 of the PD 180 may be required to acknowledge the sanitization message (or take some other action, such as sanitizing the PD 180) before the management client 118 allows the PD 180 to resume normal operation. In some embodiments, certain sanitization messages may prevent the PD 180 from being operated (e.g., lock and/or power down the PD 180 until a certain action is taken, such as performing a sanitization operation on the PD 180). The management client 118 may display other sanitization messages in a non-intrusive manner (e.g., in a way that does not interrupt operation of the PD 180). Such sanitization messages may be displayed as background notifications, non-modal prompts, and/or the like.

The sanitization manager 110 may be further configured to manage sanitization of a "dumb" PD 180. As used herein, a "dumb" PD 180 refers to a PD 180 that is not capable of running and/or hosting (and/or configured to run or host) the management client 118 (e.g., may comprise a stethoscope, reflex hammer, pulse oximetry device, recording device, notation device, and/or the like). The PD 180B shown in FIG. 1 may comprise a dumb PD 180. The PD 180B may be assigned a device identifier 181 (and be associated with a user 182B), as disclosed herein.

The sanitization stations 150 may be configured to perform sanitization operations on the PD 180. Performing a sanitization operation on a PD 180 may comprise enclosing the PD 180 within an interior compartment of the sanitization station 150, and configuring the sanitization station 150 to perform a sanitization operation on the enclosed PD 180. The users 182 may be prompted to perform sanitization operations on the respective PD 180 in response to sanitization messages from the sanitization manager 110. In some embodiments, the sanitization stations 150 comprise and/or are assigned respective identifiers 151 and are configured to maintain persistent configuration and/or logging information 153. The persistent configuration and/or logging information may comprise a configuration of the sanitization station 150, which may include, but is not limited to: the sanitization station identifier 151, name, location, status, maintenance history, sanitization records, and/or the like.

The sanitization management server 111 may further comprise the monitor 112, which may be configured to, inter alia, capture the monitoring metadata 113 pertaining to the respective PD 180. The monitor 112 may capture the monitoring metadata 113 pertaining to the PD 180 by use of, inter alia, one or more monitor units 120A-N. The monitor units 120A-N may be configured to capture particular types of the monitoring metadata 113 and/or capture the monitoring metadata 113 pertaining to the particular PD 180. The monitor units 120A-N may be further configured to communicate the monitoring metadata 113 acquired thereby to the sanitization manager 110 (via the one or more communication networks 102). Alternatively, or in addition, the monitor units 120A-N may be configured to record the monitoring metadata 113 on non-transitory storage, which may be pulled therefrom by the sanitization manager 110.

The monitor units 120A-N of the FIG. 1 embodiment may include, but are not limited to: device monitors 120A, electronic monitoring devices 120B, sanitization station monitors 120C, network monitors 120D, building monitors 120E, and so on, including health care system (HCS) monitors 120N, and so on. The monitor 112 may further comprise a correlation monitor unit 120X, which may be configured to derive the monitoring metadata 113 from the monitoring metadata 113 captured by other monitor units 120A-N. As disclosed in further detail herein, the sanitization management server 111 may be configured to generate the sanitization management data 133 for the respective PD 180, which may be configured to ensure that the PD 180 complies with a sanitization policy 119 (based on the determined sanitization state of the PD 180). The sanitization management data 133 may comprise sanitization messages configured to: indicate the sanitization status of the one or more PDs 180, identify the user(s) 182 responsible for sanitizing the respective PDs 180, indicate location(s) of the sanitization stations 150 for use in sanitizing the PD 180 (e.g., may comprise a map and/or navigation link corresponding to the nearby sanitization stations 150), require sanitization of a particular PD 180 by specified times, require immediate sanitization of a particular PD 180, and/or the like. The sanitization management data 133 may be sent to the one or more monitor units 120A-N, sanitization stations 150, users 182, PD 180, communication devices 183, and/or the like. The sanitization management data 133 may comprise any suitable electronic data including, but not limited to: text communication data, audio communication data, visual communication data, haptic feedback data, email communication data, Hyper Text Transfer Protocol (HTTP) communication data (e.g., data in Hyper Text Markup Language (HTML) format), firmware, device configuration data, application configuration data, executable code, computer-executable instructions, authentication credential(s), and/or the like. The sanitization management data 133 (and/or portions thereof) may be configured for display on one or more of: the monitor unit(s) 120A-N, the PD 180 (e.g., by use of the management client 118), the one or more communication devices 183, and/or the like. Alternatively, or in addition, the sanitization management data 133 may comprise configuration data and/or instructions configured to cause the PD 180 to perform sanitization management operations, which may include, but are not limited to: displaying a sanitization schedule for the PD 180 (in accordance with the determined sanitization state of the PD 180 and/or sanitization policy 119), display sanitization messages, implement "modal" sanitization messages (e.g., messages that a user 182 must interact with before resuming normal operation), present audible notification and/or alarms, lock the PD 180, and/or the like.

The device monitors 120A may be configured to be attached to and/or operate on respective PDs 180. In some embodiments, a device monitor 120A comprises a component of the management client 118, disclosed above. In such embodiments, the device monitor 120A may be configured to capture information pertaining to a particular "smart" PD 180. Such information may include, but is not limited to: the device identifier 181 (e.g., a unique identifier assigned to the particular PD 180); information pertaining to the users 182 of the PD 180 (e.g., user identifiers, roles, schedules, and/or the like); information pertaining to user interaction with the PD 180, user inputs to HMI components of the PD 180, and user interaction with other application(s) 184 operating on the PD 180; information accessed, updated, recorded, searched, and/or retrieved at the PD 180; location(s) of the PD 180 (e.g., information captured by location sensors of the PD 180); and so on. Alternatively, or in addition, a device monitor 120A may be configured to monitor a "dumb" PD 180, such as the PD 180B. In such embodiments, the device monitor 120A may be configured to report information pertaining to the PD 180 to other monitor units 120B-N. The device monitor 120A may, for example, comprise an radio frequency identifier (RFID) tag configured to communicate the device identifier 181 of the "dumb" PD 180. Alternatively, or in addition, a PD 180 may be monitored by an electronic monitoring device 120B, which may be configured to acquire monitoring data pertaining to the PD 180, as disclosed herein. The electronic monitoring device 120B may be embodied as a separate, independent device (e.g., separate from the PD 180 being monitored thereby). As illustrated in FIG. 1, an electronic monitoring device 120B may be configured to monitor the "dumb" PD 180B. The electronic monitoring device 120B may comprise an attachment member 190 to physically attach and/or couple the electronic monitoring device 120B to the PD 180B. In some embodiments, the attachment member 190 is configured to prevent the electronic monitoring device 120B from being removed and/or decoupled from the PD 180B (e.g., may comprise a lock). The electronic monitoring device 120B may comprise a processor 191, memory 192, non-transitory storage 193, HMI components 194, network interface components 195, and/or the like, as disclosed herein. The network interface components 195 may be configured to communicatively couple the electronic monitoring device 120B to the network(s) 102, sanitization manager 110, sanitization management server 111, and/or health care management system 103, as disclosed herein. The non-transitory storage 193 may comprise instructions configured to cause the processor 191 to perform operations, as disclosed herein. The non-transitory storage 193 may further comprise information pertaining to the PD 180 being monitored. In the FIG. 1 embodiment, the non-transitory storage 193 comprises the device identifier 181 of the PD 180B. The electronic monitoring device 120B may be configured to acquire monitoring data by use of the HMI components 194 and/or monitoring units 196. The monitoring units 196 may include, but are not limited to: location sensors (e.g., Global Positioning System (GPS) devices, RFID readers, and/or the like), device monitors (e.g., accelerometers, radiation detectors, and/or the like), and so on. The electronic monitoring device 120B may be configured to acquire monitoring information pertaining to the PD 180B by use of the monitoring units 196 and/or may prompt the users 182 for monitoring information by use of one or more of the HMI components 194. The electronic monitoring device 120B may be configured to communicate captured monitoring information to the sanitization manager 110 via the network 102 and/or record the monitoring information on the non-transitory storage 193. The electronic monitoring device 120B may be further configured to receive sanitization management information.

The sanitization station monitors 120C may be configured to capture the monitoring metadata 113 pertaining to sanitization operations performed at respective sanitization stations 150. In some embodiments, each sanitization station 150 may comprise, and/or be communicatively coupled to, a respective sanitization station monitor 120C. The sanitization station monitors 120C may capture the monitoring metadata 113 pertaining to sanitization operations performed at respective sanitization stations 150. The monitoring metadata 113 captured by the sanitization station monitors 120C may, therefore, comprise sanitization records, each sanitization record indicating that a specified PD 180 was sanitized at a designated sanitization station 150 at a particular time. The sanitization records may further include a device identifier 181 of the PD 180, an identifier 151 of the sanitization station 150, configuration and/or logging information 153 maintained by the sanitization station 150, a location of the sanitization station 150, an identifier of the user 182 who performed the sanitization operation, a duration of the sanitization operation, a type of sanitization operation (e.g., quick, standard, deep, or the like), an indication of whether the sanitization operation was fully completed, the time the sanitization operation was initiated, the time the sanitization operation was completed, diagnostics pertaining to the PD 180 and/or sanitization station 150, an authentication credential, a signature, and/or the like.

The network monitor 120D may be configured to capture the monitoring metadata 113 pertaining to network activity of the PD 180. The network monitors 120D may comprise the one or more electronic monitoring devices 120B, filters, and/or applications 184 communicatively coupled to one or more of the communication networks 102. The network monitors 120D may comprise general-purpose network monitors, such as a sniffer, packet capture device, and/or the like. Alternatively, or in addition, the network monitors 120D may comprise and/or be communicatively coupled to other network components such as network proxy servers, which may be configured to receive, process, and/or forward network traffic to and/or from the PD 180. The monitoring metadata 113 captured by the network monitors 120D may include, but is not limited to: network activity of the PD 180; information accessed, updated, recorded, retrieved, and/or searched by the PD 180; network location(s) of the PD 180 (e.g., network addresses assigned to the PD 180 and/or network interface components 195); and so on.

The building monitors 120E may be configured to capture the monitoring metadata 113 pertaining to particular building location(s) of the respective PD 180 (e.g., specific office, examination room, laboratory, and/or the like). The building monitors 120E may be configured to capture location information at a lower granularity than the device monitor 120A and/or network monitor 120D. The building monitors 120E may comprise one or more low-range communication devices, such as Bluetooth® communication devices, near-field communication (NFC) communication devices, RFID devices, bar code scanners, and/or the like. The building monitors 120E may capture the device identifier 181 of the PDs 180 when such PDs 180 enter and/or exit particular building locations (e.g., rooms, offices, examination rooms, labs, operating rooms, and/or the like). The building monitors 120E may capture the device identifiers 181 using any suitable mechanism including, but not limited to: scanning a barcode and/or QR code on the PD 180 (and/or presented on a display of the PD 180), reading an RFID tag on the PD 180, and capturing the device identifier 181 via Bluetooth®, NFC, and/or the like. The building monitors 120E may be further configured to monitor the time the PD 180 remains in particular locations (e.g., track the time the PD 180 enters and exits particular building locations).

The HCS monitors 120N may be configured to capture the monitoring metadata 113 pertaining to health care activities, which may include, but is not limited to: health care information accessed, updated, recorded, retrieved, and/or searched on the PD 180; health care-related tasks performed at the PD 180, scheduled tasks of the user 182 of the PD 180, user interaction with the health care management system 103, and/or the like. The HCS monitors 120N may be incorporated into the health care management system 103 (e.g., may comprise an add-on and/or component of the health care management system 103).

Alternatively, or in addition, the HCS monitors 120N may be configured for operation on the sanitization manager 110, sanitization management server 111, and/or PD 180. An HCS monitor 120N operating on the sanitization manager 110 and/or sanitization management server 111 may be configured to access information pertaining to the PD 180 and/or user 182 maintained by the health care management system 103 (e.g., may comprise an integration component configured to use the health care management system 103). An HCS monitor 120 operating on the PD 180 may be configured to monitor user interaction with client-side components of the health care management system 103 (e.g., a health care management application operating on the PD 180).

In some embodiments, the monitor 112 comprises the correlation monitor unit 120X configured to identify and/or derive additional monitoring metadata 113 from the monitoring metadata 113 captured by respective monitor units 120A-N. The correlation monitor unit 120X may comprise correlation rules, which may define mechanisms for identifying and/or deriving additional monitoring metadata 113 from the monitoring metadata 113 acquired by monitor units 120A-N.

Figure 2:
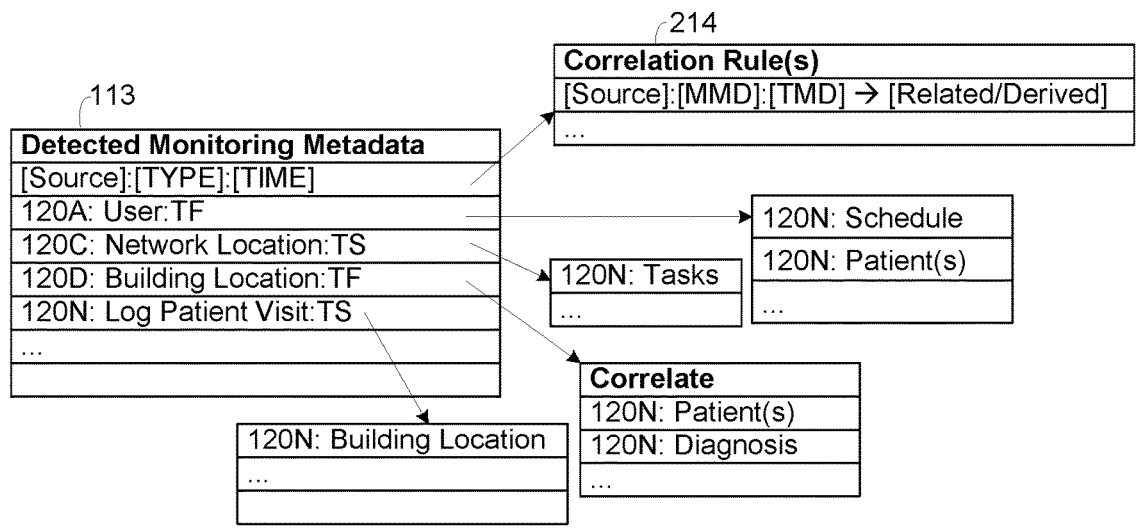
FIG. 2 depicts embodiments of monitoring metadata correlation rules.

FIG. 2 depicts exemplary embodiments of correlation rules 214 for use in identifying and/or driving additional monitoring metadata 113 from the monitoring metadata 113 acquired by the monitor units 120A-N, as disclosed herein. The correlation rules 214 may be maintained within the non-transitory data store 114 of the sanitization manager 110, as disclosed herein. The monitoring metadata 113 may be received at the sanitization manager 110 via one or more network(s) 102 and/or stored within the non-transitory data store 114. The correlation rules 214 of the FIG. 2 embodiment may be defined in terms of source, type, and time (e.g., time stamp and/or timeframe). The source may identify the monitor unit(s) 120A-N that acquired the monitoring metadata 113, the PD 180 and/or the users 182 to which the monitoring metadata 113 pertains, and so on. By way of example, a correlation rule 214 may operate on the monitoring metadata 113 pertaining to a particular user 182 during a particular timeframe. The correlation rule 214 may obtain additional monitoring metadata 113 based on the determined user 182 by, inter alia, using the HCS monitor 120N to access the schedule of the user 182 and/or patients examined by the user 182 during the specified timeframe. The additional monitoring metadata 113 may indicate whether the PD 180 was exposed to particular contaminants during use (e.g., the patients examined by the user 182 were diagnosed with particular communicable diseases). Another correlation rule 214 may operate on network location information (e.g., network location during a specified timeframe as determined by a network monitor 120D). The correlation rule 214 may use the HCS monitor 120N to associate the network location with a particular location and/or health care-related task performed during the specified timeframe. In another example, a correlation rule 214 may use the building location of the PD 180 during a particular timeframe (as determined by a building monitor 120E) to identify the patient(s) who were in the vicinity of the PD 180, which may be used to derive additional monitoring metadata 113 for the PD 180 (e.g., may indicate that the PD 180 was exposed to particular contaminants based on the medical condition of the identified patients). In yet another example, a correlation rule 214 may augment the monitoring metadata 113 pertaining to a patient visit obtained by use of an HCS monitor 120N with additional monitoring metadata 113 indicating the building location of the PD 180 during the patient visit (based on information pertaining to the patient visit obtained from the health care management system 103). Although particular examples of the correlation rules 214 are described herein, the disclosure is not limited in this regard and could be adapted to use any suitable technique for identifying and/or deriving additional monitoring metadata 113 from the monitoring metadata 113 acquired by the monitor units 120A-N.

Referring back to FIG. 1, the sanitization manager 110 may comprise a sanitization policy manager 116, which may be configured to: a) acquire the monitoring metadata 113 pertaining to a PD 180 (by use of the monitor 112), and b) evaluate a sanitization policy 119 assigned to the PD 180 to, inter alia, determine a PD state 117 of the PD 180. The sanitization manager 110 may be further configured to implement one or more management actions configured to ensure that the PD 180 complies with the sanitization policy 119. The management actions may comprise generating the sanitization management data 133 pertaining to the PD 180, as disclosed herein.

Figure 3:
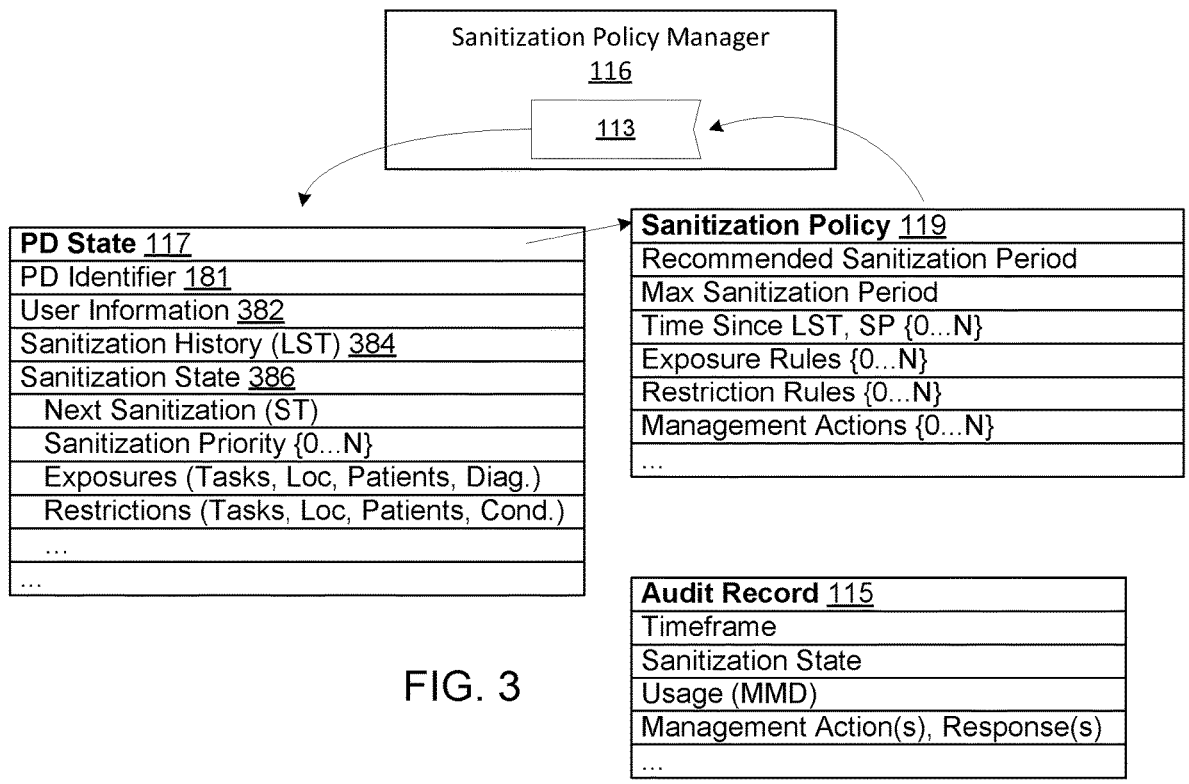
FIG. 3 depicts embodiments of a sanitization policy.

FIG. 3 depicts one embodiment of a sanitization policy manager 116 configured to use the monitoring metadata 113 pertaining to a PD 180 to determine the PD state 117 of the PD 180. As illustrated in FIG. 3, the sanitization policy manager 116 may receive the monitoring metadata 113. The monitoring metadata 113 may include the monitoring metadata 113 acquired by the one or more monitor units 120A-N and/or additional monitoring metadata 113 identified and/or derived therefrom, as disclosed herein. The sanitization policy manager 116 may be configured to aggregate the monitoring metadata 113 in the non-transitory data store 114, which may comprise combining, filtering, coalescing, categorizing, and/or otherwise processing the monitoring metadata 113. The sanitization policy manager 116 may use the monitoring metadata 113 pertaining to a particular PD 180 to determine a PD state 117 of the particular PD 180 (based on a sanitization policy 119). The PD status 117 may comprise any suitable information pertaining to a PD 180 including, but not limited to: a device identifier 181, user information 382, sanitization history information 384, sanitization state 386 information, and so on. The user information 382 may comprise information pertaining to the users 182 of the PD 180, which may include, but is not limited to: the users 182 of the PD 180 during particular timeframes, the users 182 assigned to maintain the PD 180, the users 182 assigned to sanitize the PD 180, user roles associated with the PD 180, location(s) assigned to the PD 180, building location(s) assigned to the PD 180, organizational groups associated with the PD 180, and/or the like. The sanitization history information 384 may comprise information pertaining to sanitization operations performed on the PD 180, which may include, but is not limited to: information pertaining to the last sanitization operation performed on the PD 180, including the last sanitization time (LST) for the PD 180; information pertaining to the sanitization station(s) 150 used to sanitize the PD 180; diagnostic information pertaining to the sanitization operations (e.g., sanitization records); and/or the like. The LST of the PD 180 may comprise a timestamp at which the sanitization policy manager 116 verified successful completion of a sanitization operation on the PD 180 at a sanitization station 150. The sanitization state 386 of the PD 180 may comprise information pertaining to upcoming sanitization operations required in order for the PD 180 to comply with the sanitization policy 119. The sanitization state 386 may include, but is not limited to: a schedule for a next sanitization operation to be performed on the PD 180 (e.g., a next sanitization time) for the PD 180), a priority for the next sanitization operation, and information pertaining to potential contamination of the PD 180 (e.g., potential contamination since the last sanitization operation PD 180 was performed on the PD 180).

The sanitization priority of the PD state 117 may indicate a relative priority of the next sanitization operation scheduled for the PD 180. The sanitization priority may range from a low sanitization priority (e.g., 0) to a high sanitization priority (e.g., 100). A low sanitization priority may indicate that the PD 180 is currently in compliance with the sanitization policy 119 (e.g., does not need to be sanitized until a future time). Higher sanitization priorities may indicate that compliance with the sanitization policy 119 requires a sanitization operation to be performed relatively soon (e.g., the next sanitization time is less than a threshold). A high sanitization priority may be assigned when the PD 180 is due for sanitization. Critical sanitization priorities may be assigned when the PD 180 is out of compliance with the sanitization policy 119 (e.g., the next sanitization operation is past due), the PD state 117 indicates that the PD 180 may have been exposed to particular contaminants (e.g., *Staphylococcus* bacteria), a request to force sanitization of the PD 180 was received at the sanitization manager 110, and/or the like.

The exposure information of the PD state 117 may be based on any of the monitoring metadata 113 disclosed herein (e.g., based on potential exposures since the LST of the PD 180). The information pertaining to potential contamination of the PD 180 may include, but is not limited to: information pertaining to potential exposure to contamination based on tasks associated with the PD 180 (e.g., exposures while performing tasks since the LST, such as a task to culture particular strains of bacteria), information pertaining to potential exposure to contamination based on location(s) of the PD 180 since the LST (e.g., particular examination rooms, laboratories, patient wards, and/or the like), information pertaining to potential exposure to contamination based on patients examined and/or treated since the LST (e.g., indicate that the PD 180 was used during examination and treatment of a patient who was subsequently diagnosed with a particular condition, such as a staph infection), and/or the like.

The sanitization state 386 may further specify one or more device restrictions for the PD 180. As used herein, a "device restriction" means restriction on permitted usage of the PD 180. The device restrictions may be determined based on the monitoring metadata 113 pertaining to the PD 180 (e.g., time since LST, potential exposure to contamination, and soon), and restriction rules of the sanitization policy 119, as disclosed in further detail herein. A device restriction may pertain to any suitable usage characteristic of the PD 180 including, but not limited to: a task restriction, a location restriction, a patient restriction, a patient condition restriction, and/or the like. A task restriction may be configured to prevent the PD 180 from being used for specified tasks. A location restriction may be configured to prevent the PD 180 from certain location(s) (e.g., prevent the PD 180 from entering a ward used to house patients with compromised immune systems). A patient and/or patient condition restriction may be configured to prevent the PD 180 from being used to examine, treat, or diagnose particular patients and/or patients associated with specified conditions or diagnoses. The restriction rules may be configured to prevent the PD 180 from being used for certain tasks, in certain location(s), and/or with certain patients while the PD 180 is in a particular sanitization state 386 (e.g., after potential exposure to *Staphylococcus* bacteria and/or after expiration of the maximum sanitization period). Accordingly, the device restrictions may be configured to prevent a PD 180 that was potentially exposed to a highly contagious contaminant from being used in a manner likely to spread the contaminant within a venerable population. The device restrictions may be removed after the PD 180 is sanitized.

The sanitization policy manager 116 may determine the PD status 117 based on a current PD status 117 of the PD 180 (if any), the monitoring metadata 113 pertaining to the PD 180, and the sanitization policy 119. In some embodiments, the sanitization policy manager 116 may comprise a plurality of different sanitization policies 119, which may be assigned to respective PDs 180, users 182, roles, and/or groups (based on the device identifier 181 and/or user information 382, role, and/or the like). In some embodiments, the sanitization policy manager 116 updates the PD status 117 of a PD 180 periodically, regardless of whether the monitoring metadata 113 pertaining to the PD 180 is received. Alternatively, or in addition, the sanitization policy manager 116 may be configured to update the PD status 117 of a PD 180 in response to receiving the monitoring metadata 113 pertaining to the PD 180 (via the monitor 112). The sanitization policy manager 116 may determine the PD status 117 of a PD 180 based on the sanitization policy 119 assigned to the PD 180, which may include, but is not limited to: a recommended sanitization period, a maximum sanitization period, a time since LST, exposure rules, restriction rules, management actions, and so on.

The recommended sanitization period may specify a recommended time between sanitization operations on the PD 180 (e.g., weekly, daily, hourly, or the like). The maximum sanitization period may indicate a maximum time between sanitization operations. The time since LST may assign respective sanitization priorities (e.g., 0 . . . N) based on the time elapsed since the LST on the PD 180. The sanitization policy 119 may further comprise exposure rules, which may trigger sanitization of the PD 180 regardless of the time elapsed since the LST (and assign a corresponding sanitization priority). The exposure rules may pertain to tasks in which the PD 180 was used, locations of the PD 180, patient(s), patient diagnosis, and so on, as disclosed above. The exposure rules pertain to potential exposures determined from the monitoring metadata 113 pertaining to the PD 180, as disclosed herein. The exposure rules may assign different sanitization priorities to different respective potential exposure events. For example, the sanitization policy 119 may comprise a task-based exposure rule specifying that, if the monitoring metadata 113 and/or PD state 117 indicates that the PD 180 was used to perform a task associated with a high likelihood of contamination (e.g., examination of a contagious patient diagnosed with a staph infection), the sanitization state 386 of the PD 180 is set to "contaminated" and is scheduled for immediate sanitization (at a high priority), regardless of LST of the PD 180. A location-based exposure rule may require the PD 180 to be sanitized after being used in particular locations (e.g., after being used in particular examination rooms, wards, laboratories, and/or the like), regardless of the LST of the PD 180. Similarly, patient- and/or diagnosis-based exposure rules may specify that the PD 180 is to be sanitized after being exposed to particular patients and/or exposed to patients with particular conditions, regardless of LST. The exposure rules may assign different sanitization priorities to different exposure events. For example, an exposure rule for potential exposure to a patient with a highly contagious flesh-eating bacteria may be assigned the highest sanitization priority (e.g., 100), configured to lock and/or disable the PD 180 until a "deep" sanitization operation is successfully completed on the PD 180. By contrast, an exposure rule pertaining to potential exposure to a patient diagnosed with a more benign condition may correspond to a lower sanitization priority (e.g., may move up the scheduled time for the next sanitization operation, but not require immediate sanitization).

The sanitization policy 119 may further comprise restriction rules. The restriction rules may be used to determine device restrictions for the PD 180. As disclosed above, the device restrictions may be configured to prevent the PD 180 from being used for specified tasks, in specified locations, with specified patients and/or with patients having specified conditions. The restriction rules may be configured to impose one or more device restrictions on the PD 180 based on the time since LST. For example, the restriction rules may generate a restriction rule configured to prevent the PD 180 from being used within a neonatal clinic if the recommended sanitization period for the PD 180 has expired. In another example, the restriction rules may generate restriction rules to prevent the PD 180 from being used with patients with compromised immune systems in response to determining that the PD 180 was potentially exposed to patients diagnosed with one or more communicable diseases.

The sanitization policy 119 may be further configured to adapt the sanitization state 386 in accordance with predicted usage patterns of the PD 180. For example, the PD 180 may be provisioned to a user 182 assigned to care for patients with compromised immune systems. The sanitization policy 119 assigned to the user 182 may, therefore, require immediate sanitization of the PD 180 after any potential exposure event (e.g., exposure due to a task, location, patient, and/or diagnosis, as disclosed herein). Moreover, restriction rules of the sanitization policy 119 may prevent the PD 180 from being used with the patients until the PD 180 is sanitized. The sanitization policy 119 assigned to a different user 182 assigned to work with patients that are generally healthy may allow longer time periods between sanitization and may comprise exposure rules that assign lower priorities to potential exposure events (and specify more lenient restriction rules).

In some embodiments, the sanitization policy manager 116 may be configured to weigh and/or combine time-based policy considerations with exposure-based policy considerations to determine the overall sanitization state 386 for the PD 180 (e.g., determine the next sanitization time and sanitization priority for the PD 180, impose device restrictions, and so on). In some embodiments, the sanitization policy manager 116 is configured to increase a time-based sanitization priority assigned to the PD 180 based on one or more exposure rules (e.g., increase a sanitization priority for the PD 180 and/or decrease the recommended sanitization period in response to one or more exposure events). Similarly, the sanitization priority assigned to a particular exposure event by an exposure rule may be adjusted in accordance with the time since the LST (e.g., adjusted upwards for higher elapsed time since LST and vice versa).

The monitoring metadata 113 evaluated by the sanitization policy manager 116 may include the monitoring metadata 113 pertaining to sanitization operations performed on the PD 180. As disclosed above, when a PD 180 is sanitized at a sanitization station 150, the sanitization station 150 may be configured to capture and/or record information pertaining to the sanitization operation, including the device identifier 181 of the PD 180 being sanitized (e.g., produce a sanitization record, as disclosed herein). The monitoring metadata 113 pertaining to the sanitization operation may be captured by a sanitization station monitor 120C and transmitted to the sanitization manager 110, as disclosed herein. In response, the sanitization policy manager 116 may update the PD state 117 of the PD 180 to indicate that the sanitization operation was performed, which may comprise updating the sanitization history information 384 of the PD state 117, including the LST; determining a next sanitization time for the PD 180 based on the recommended and/or maximum sanitization period of the sanitization policy 119; and so on. The sanitization policy manager 116 may be further configured to reset exposure information pertaining to the PD 180 (and/or indicate that the PD 180 was sanitized after the potential exposures) and/or remove device restrictions from the PD 180 (and/or indicate that the device restrictions were imposed before the LST). The sanitization policy 119 may define one or more management actions. The management actions may be configured to facilitate compliance with the sanitization policy 119. The management actions may be configured to ensure that the PDs 180 are sanitized in accordance with the sanitization policy 119 (e.g., based on the determined sanitization state 386 of the PD 180). The management actions may comprise generating and/or transmitting the sanitization management data 133 to the one or more monitor units 120A-N, the sanitization stations 150, the users 182, the PD 180, the communication devices 183, and/or the like, as disclosed herein. The sanitization management data 133 may be configured to prompt, remind, direct, command, and/or require the users 182 to sanitize the PD 180 in accordance with the determined PD state 117 thereof. The sanitization manager 110 may configure the sanitization management data 133 in accordance with the sanitization priority of the PD state 117. The sanitization management data 133 generated for a PD 180 having a relatively low sanitization priority (e.g., a PD 180 that is within the recommended sanitization period, with few potential exposure events) may comprise a low priority message configured to remind the user 182 of the PD 180 of an upcoming sanitization operation scheduled for the PD 180. The management client 118 and/or electronic monitoring device 120B may be configured to present the lower-priority sanitization messages unobtrusively and without interfering with normal operation of the PD 180.

The sanitization manager 110 may adapt the sanitization management data 133 in accordance with the sanitization priority of the PD state 117. The sanitization management data 133 generated for a PD 180 that is nearing its scheduled sanitization time may comprise medium priority reminder message(s). The management client 118 and/or electronic monitoring device 120B may be configured to present medium priority sanitization messages in the foreground, such that the user 182 of the PD 180 must acknowledge and/or dismiss such messages before continuing to use the PD 180. Management actions for high sanitation priorities (e.g., indicating that the next sanitization operation is due, or past due) may comprise generating the sanitization management data 133 comprising sanitization commands and/or directives. The management client 118 and/or electronic monitoring device 120B may be configured to present information pertaining to such commands and/or directives interstitially and/or modally such that the user 182 is locked out of the PD 180 while such commands and/or directives are displayed. The management client 118 may require the user 182 to acknowledge the commands and/or directives (e.g., agree to sanitize the PD 180 as soon as practical) before being allowed to continue using the PD 180. The sanitization management data 133 may be further configured to notify the user 182 and/or persons in the vicinity of the PD 180 that the PD 180 is out of compliance, which may comprise producing an audible alert notification at the PD 180, generating haptic feedback at the PD 180, causing the PD 180 to display a compliance message, and/or the like.

The management client 118 and/or electronic monitoring device 120B may be configured to deactivate the alerts in response to the user 182 acknowledging and/or responding to the sanitization command and/or directive. The alerts may be reasserted if the PD 180 has not been sanitized within a predetermined time period.

Management actions for the highest sanitization priorities (e.g., when the PD 180 is past due for sanitization by more than a threshold and/or after specified exposure events) may comprise generating the sanitization management data 133 comprising a sanitization imperative. The sanitization imperative may comprise configuration data, instructions, code, and/or other data configured to block normal operation of the PD 180. The sanitization imperative may be configured to lock the PD 180 until the PD 180 is sterilized. The sanitization imperative may be further configured to notify the user 182 (and persons in the vicinity of the PD 180) that the PD 180 is out of compliance with the sanitization policy 119, as disclosed above.

The management actions may further specify sending notifications to other personnel, such as compliance personnel, management, maintenance staff, administrative staff, support staff, and/or the like (via the communication device(s) 183). The notifications may identify the PD 180 that is scheduled (or past due) for sanitization, identify the users 182 of the PD 180 (and/or the users 182 assigned to sanitize the PD 180), specify the location of the PD 180, and so on. The other personnel may facilitate sanitization of the PD 180 in response to the notifications.

The sanitization management data 133 disclosed herein may include information configured to facilitate sanitization of the PD 180, which may include, but is not limited to: directions to nearby sanitization stations 150, instructions for the proper use of the sanitization stations 150, and information pertaining to the PD state 117 (e.g., time elapsed since the LST, potential exposure events, device restrictions, and so on). The sanitization management data 133 may further comprise notification messages directed to other personnel, such as compliance personnel, management, maintenance staff, administrative personnel, support staff, and/or the like.

In some embodiments, the sanitization policy manager 116 may be further configured to maintain audit records 115. The audit records 115 may track the PD state 117 of the respective PD 180 (e.g., track the timeframe between a first sanitization operation performed on the PD 180 and a subsequent second sanitization operation performed on the PD 180). An audit record 115 may include, but is not limited to: the timeframe covered by the audit record 115, the PD state 117 during the timeframe (e.g., assigned sanitization priorities, exposure events, device restrictions, and so on), usage of the PD 180 during the timeframe (based on the monitoring metadata 113), management actions taken and/or responses to such management actions, and so on. The management actions may specify the sanitization management data 133 generated for the PD 180, as disclosed herein. The management actions may specify the messages, notifications, commands, directives, and/or imperatives for the PD 180 during the timeframe (and actions taken by the users 182 in response, such as acknowledgment of sanitization commands, directives, and/or the like).

As disclosed above, the monitoring metadata 113, audit records 115, PD state 117, sanitization policy 119, correlation rules 214, and other data pertaining to the sanitization manager 110 may be maintained within the non-transitory data store 114. In addition, instructions comprising the sanitization manager 110, monitor 112, sanitization policy manager 116, management client 118 (disclosed in further detail herein), one or more of the monitor units 120A-N, the correlation monitor unit 120X, the management client 118, and the like may be stored on the non-transitory data store 114 (or other non-transitory storage devices).

Figure 4A:
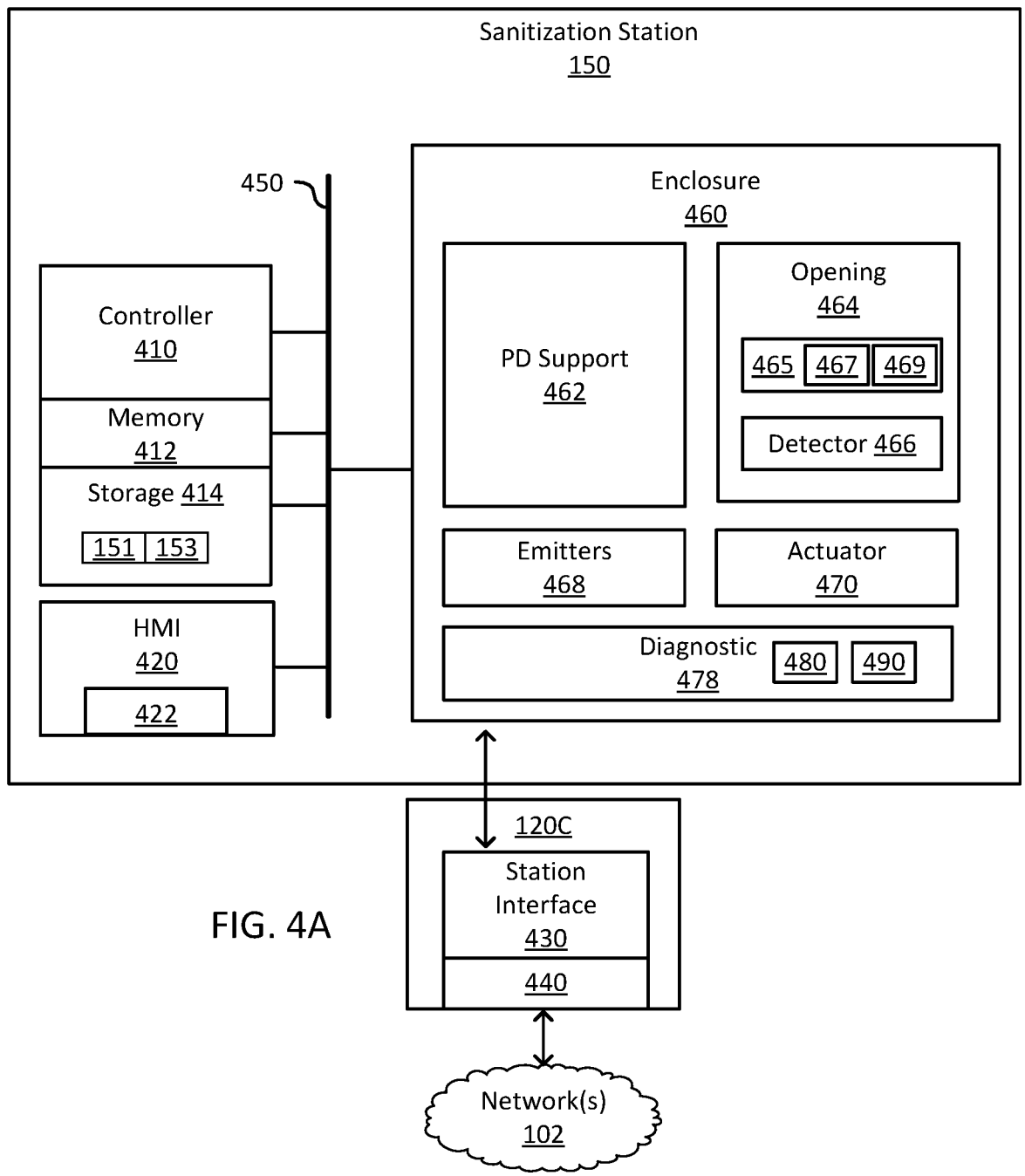
FIG. 4A is a schematic block diagram of one embodiment of a sanitization station.

FIG. 4A is a schematic block diagram of one embodiment of a sanitization station 150. As disclosed above, the surfaces of a PD 180 may attract and/or harbor contaminants, such as potentially harmful organisms (e.g., microbes, pathogens, viruses, bacteria, and/or the like). In some embodiments, the sanitization station 150 is configured to sanitize the PD 180 by use of electro-optical (EO) radiation. As used herein, EO radiation or "sanitizing EO radiation" refers to any suitable wavelength and/or type of EO radiation capable of sanitizing a surface; such radiation may include, but is not limited to: type C ultraviolet radiation (UV-C) comprising wavelengths between 280 and 100 nm, type B ultraviolet radiation (e.g., UV-B), middle ultraviolet radiation (MUV), far ultraviolet radiation (FUV), ionizing EO radiation, non-ionizing EO radiation, a combination of wavelengths and/or EO radiation types, or the like.

The sanitization station 150 disclosed herein may be configured to irradiate a PD for different amounts of time. Some types of EO radiation may be capable of sanitizing the surface of a PD 180 relatively quickly (e.g., three to five minutes of exposure to UV-C may be sufficient to sanitize a surface). In some embodiments, the EO radiation exposure time may be configured or adapted in accordance with the intensity of the emitted EO radiation, type(s) of EO radiation used to irradiate the PD 180, user configuration and/or preferences, or the like. In some embodiments, the amount of EO exposure is configurable by a user (e.g., via button, selector, timer, or other human-machine-interface component). Alternatively, or in addition, the amount of exposure may be automatically determined based upon properties of the EO radiation, time since a last sanitization cycle for the PD 180, and/or other suitable factors. In another embodiment, the amount of EO exposure for a PD 180 may be based on the sanitization state 386 of the PD 180 (e.g., the time elapsed since the LST, exposure(s) since the LST, and/or the like).

In some embodiments, the sanitization station 150 may be configured to sanitize a PD 180 using a single wavelength of sanitizing EO radiation. In other embodiments, multiple wavelengths of EO radiation may be used, comprising a composite emission of sanitizing EO radiation. In some embodiments a series of different wavelengths of sanitizing EO radiation may be applied according to a particular sequence or pattern. Where multiple wavelengths of sanitizing EO radiation are used, the particular wavelengths applied to the PD 180 may be configured to target a specific organism (e.g., a specific type of bacteria). The particular wavelength may also be selected to avoid damage to the PD 180 (e.g., may be selected to avoid damaging the finish, materials, case, and/or operational components of the PD 180). For example, the EO radiation wavelengths may be selected such that the EO radiation will sanitize the surface of the PD 180, while minimizing harm to the plastics, composites, metals, alloys, fabrics, pigments, or dyes used in the construction of the PD 180. In some embodiments, wavelengths may be selected to minimize penetration of the EO radiation into the interior of the PD 180 and/or wavelengths that will not adversely affect the electronics, processor, memory, storage, and/or other components of the PD 180.

The sanitization station 150 disclosed herein may be configured to sanitize any number of different types of the PD 180, including, but not limited to: a tool, a diagnostic device, a portable examination device (e.g., a stethoscope, reflex hammer, pulse oximetry device, and/or the like), a portable treatment device, a portable communication device, a phone, a wireless headset, a mobile phone, a smart phone, a portable notation device, a portable media device, an image capture device, a video capture device, an audio capture device, a portable computing device, a tablet computing device, a laptop computer, a notebook computer, an electronic reading device, a personal digital assistant (PDA), a palmtop computer, a handheld computer, a pen computer, an ultra-mobile personal computer, a pager, a portable navigation device, a personal navigation assistant (e.g., portable GPS unit), and/or the like.

The sanitization station 150 may comprise an interior enclosure or compartment configured to receive a PD 180 and one or more EO emitters. The apparatus may further comprise a support member configured to maintain the PD 180 at a particular orientation and/or position within the enclosure. In some embodiments, the support member may be transparent (or substantially transparent) to the EO radiation emitted by the EO emitters and/or the interior surface of the enclosure may be configured to reflect EO radiation, such that the EO emitter is capable of irradiating the entire surface of the PD 180. The apparatus may further comprise a charging module configured to charge the PD 180 while the PD 180 is within the enclosure or compartment (and/or while the PD 180 is being sanitized by the EO radiation). The charging module may be configured to charge the PD 180, provide a data connection, and/or provide an audio connection to the PD 180. For example, the charging module may include a communication module that provides a communication link to a PD 180. Accordingly, in some embodiments, the apparatus may be configured to act as a dock for the PD 180. For example, the charging module may be coupled to a docking connector configured to couple the PD 180 to an external computing device, such as a server, personal computer, docking station, or the like. In some embodiments, the apparatus may comprise one or more indicators configured to display sanitization and/or charging status information to a user 182.

The apparatus may be configured to limit activation of the EO emitters. In some embodiments, the EO emitters may be configured to emit EO radiation in response to determining that the enclosure is in a closed configuration (e.g., is sealed). As used herein, a "closed" or "sealed" configuration refers to a configuration in which the interior region, portion, and/or compartment of the apparatus is closed with respect to the transmission of EO radiation, such that there is no optical transmission path from the interior of the apparatus to the exterior of the apparatus and/or EO radiation of the emitter is not radiated to the exterior of the apparatus (e.g., the EO radiation does not escape the interior compartment). By contrast, in an "open" configuration, the interior of the apparatus is accessible, such that EO radiation emitted therein would be capable of radiating from the apparatus. In the open configuration, the PD 180 may be placed within the apparatus and/or removed from the apparatus.

In some embodiments, the PD 180 sanitization apparatus may comprise a detector module configured to determine whether the apparatus is closed. The PD 180 sanitization apparatus may be configured to activate the sanitization module (e.g., EO emitter) in response to determining that the apparatus is in a closed or sealed configuration. The sanitization module may be deactivated in response to the detector module determining that the apparatus is in an open or unsealed configuration. The detector module may comprise one or more detection mechanisms including, but not limited to: contact switches, conductive switches, magnetic switches, capacitive switches, resistive switches, latches, or the like. In some embodiments, the detector module may comprise a plurality of redundant detection mechanisms, and the sanitization module may be activated in response to each of the detection mechanisms indicating that the apparatus is in a closed or sealed configuration.

In some embodiments, the PD 180 sanitization apparatus may comprise an enclosure comprising an upper portion and a lower portion. The upper and lower portions may form a clamshell, and may define an interior portion configured to receive the PD 180. In some embodiments, an apparatus for sanitizing a portable device comprises an enclosure and a lid wherein the lid may be opened so that a PD 180 can be placed into the enclosure. In one embodiment, the apparatus comprises an enclosure and a cover that slides off or away from a base to access the enclosure. In yet another embodiment the apparatus comprises an enclosure and a drawer wherein the drawer is configured to slide or rotate out of the enclosure so that a PD 180 can be placed therein. The drawer may comprise a tray or other support member configured to receive a PD 180. In some embodiments, the tray comprises a rim, lip, or raised portion extending from the tray to prevent the PD 180 from sliding off the tray when the drawer is opened and/or closed. In one embodiment, the apparatus comprises an enclosure and one or more doors for accessing the enclosure. In one embodiment, the enclosure is within a cabinet or cart and is configured for receiving two or more PDs 180. One or more support members in the cabinet may be configured to hold the two or more PDs 180 in a particular orientation to allow sanitization of the PDs 180.

In the FIG. 4A embodiment, the sanitization station 150 comprises a controller 410, memory components 412, storage components 414, HMI components 420, and an enclosure 460. The controller 410 may include, but is not limited to: a circuit, a chip, a package, a microprocessor, a microcontroller, a central processing unit, a general-purpose processing unit, a special-purpose processing unit, processing circuitry, logic circuitry, an integrated circuit (IC), a System on a Chip (SoC), a Programmable System on a Chip (PsoC), a System in Package (SiP), an Application-specific Integrated Circuit (ASIC), configurable circuitry, programmable circuitry, a Field Programmable Gate Array (FPGA), a Complex Programmable Logic Device (CPLD), a Programmable Logic Array (PLA), and/or the like. The memory components 412 may include, but are not limited to: cache memory (on-board cache of the controller 410), volatile memory, Random-Access Memory (RAM), Dynamic RAM (DRAM), Static RAM (SRAM), Thyristor RAM (TRAM), Zero-capacitor RAM (ZRAM), and/or the like. The storage components 414 may include, but are not limited to: a non-transitory storage device, a non-transitory memory device, a solid-state memory, a hard drive, a magnetic disk storage device, an optical storage device, a tape storage device, a Flash memory, a NAND-type Flash memory, a NOR-type Flash memory, a Programmable Metallization Cell (PMC) memory, a Silicon-Oxide-Nitride-Oxide-Silicon (SONOS) memory, a Resistive RAM (RRAM) memory, a Floating Junction Gate RAM (FJG RAM), a ferroelectric memory (FeRAM), a magnetoresistive memory (MRAM), a phase change memory (PRAM), an Electrically Erasable Programmable Read-Only Memory (EEPROM), a cache storage device, a remote storage device, a Network Attached Storage (NAS) device, and/or the like. The HMI components 420 may include, but are not limited to: input/output devices, such as keyboards, buttons, switches, pointer and/or gesture devices (e.g., mouse, touch pad, touch screen, and/or the like), cameras, display devices, monitors, status indicators, static indicator lights, audio capture devices, audio output devices, haptic feedback devices, and/or the like. Interconnect components 450 may comprise any suitable circuitry for communicating data and/or commands between the components of the sanitization station 150.

The controller 410 may be configured to control the operation of the sanitization station 150, which may comprise selectively activating and/or deactivating an opening 464, emitters 468, an actuator 470, and a PD support 462. The HMI components 420 may comprise one or more input/output components, such as buttons, switches, displays, and the like. The HMI components 420 may include a status indicator configured to display and/or communicate status information pertaining to the sanitization station 150, such as current sanitization status, sanitization time, charge status, charge time, powered-on state, closure state of the enclosure 460, and so on. In some embodiments, the status indicator comprises one or more visual indicators, such as Liquid Crystal Display (LCD), one or more light emitters, or the like. The status indicator may comprise one or more acoustic indicators designed to produce sounds or speech to indicate the sanitizing and/or charging status. The acoustic indicator may be a speaker, a vibrator, or any other mechanism configured to generate vibrations or other acoustic signals. The HMI components 420 may be configured to receive user input and/or configuration information, such as sanitization time and/or mode parameters, charge settings, and so on.

The sanitization station 150 may further comprise an enclosure 460 configured to receive a PD 180 via an opening 464. The opening 464 may comprise a clamshell configuration (e.g., an upper member and a lower member), a tray, a drawer opening, a door to a cabinet interior, a retractable cover, or the like. The enclosure 460 may comprise a closed configuration and an open configuration. As described above, in the closed configuration, the enclosure 460 may be sealed with respect to EO radiation, such that EO radiation emitted therein (e.g., by the emitter 468 of the controller 410) is not emitted outside of the enclosure 460. The enclosure 460 may comprise a detector 466 configured to detect whether the enclosure 460 is in the closed configuration. The detector 466 may be configured to communicate the closure status of the enclosure 460 to the controller 410. The controller 410 may be configured to deactivate the controller 410 when the enclosure 460 is not in the closed configuration. As described above, the detector 466 may comprise one or more detection mechanisms, such as switches, latches, or the like.

The controller 410 may be configured to emit EO radiation into an interior of the enclosure 460. The EO radiation may be configured to irradiate the surface of the PD 180 within the enclosure 460. The controller 410 may be configured to emit EO radiation at one or more wavelengths, which may be configured to kill and/or render harmless organisms on the surface of the PD 180 (e.g., bacteria). In some embodiments, the controller 410 is configured to emit a single wavelength of EO radiation. In other embodiments, the controller 410 is configured to emit a broad spectrum of sanitizing EO radiation. The controller 410 may be configured to emit multiple discrete wavelengths or multiple narrow spectrums of EO radiation. In some embodiments, the controller 410 is configured to emit EO radiation at wavelengths between 240 nm and 280 nm, which may disrupt the chemical bonds of DNA and RNA, thereby killing microorganisms. Radiation emitted at these wavelengths is also known to break down organic molecules and carbon-based molecules. In some embodiments, a wavelength of the EO radiation is selected to be suitable for breaking down particles of grease or skin oil. In some embodiments, the emitted wavelengths of EO radiation are preselected. In other embodiments the emitted wavelengths are selected by the user, for example by the user selecting a set of wavelengths or indicating a choice between a plurality of preset combinations of wavelengths via the HMI components 420.

The controller 410 may comprise an emitter 468 configured to emit EO radiation of an appropriate wavelength and/or intensity to sanitize the PD 180, as described above. The emitter 468 may be located in a suitable position within the enclosure 460 so that the entire surface of the PD 180 is exposed to the EO radiation. In some embodiments, the controller 410 may comprise a plurality of the emitters 468 configured to irradiate the PD 180 from different locations, angles, and/or positions within the enclosure 460.

In some embodiments, a single emitter 468 is used, and EO radiation emitted therefrom is reflective, refracted, and/or diffused within the enclosure 460 (by an inner surface of the enclosure 460). In some embodiments, the one or more emitters 468 are located directly above or below the PD 180 and EO radiation is propagated through the interior portion by means of reflective and/or refractive surfaces. In other embodiments, the one or more emitters 468 are disposed at the side of the PD 180 and EO radiation is propagated through the enclosure 460 by means of reflective and/or refractive surfaces. In yet other embodiments, a plurality of the emitters 468 are located throughout the enclosure 460.

The emitter 468 may comprise any suitable EO radiation source, including, but not limited to, a light emitting diode (LED), a laser, an electric arc discharge, a gas-discharge lamp, a fluorescent lamp, or the like. In some embodiments, the emitter 468 is configured to be compact to minimize the size requirements of the sanitization station 150. In another embodiment, a larger dimensioned emitter(s) 468 may be used. In one embodiment, the emitter 468 includes an elongated emitter tube forming a rounded arc, such as a portion of a circle, oval, or other rounded shape. In one embodiment, the elongated emitter tube forms at least a substantial portion of one of the circle and the oval. In some embodiments, an emitter 468 comprising an arc shape, a circle shape, an oval shape, or other shape within a plane may increase uniformity with which EO radiation is distributed on a substantially parallel surface.

The emitter 468 may further comprise one or more lenses for distributing, focusing, spreading, or otherwise directing EO radiation emitted thereby to particular portions of the interior of the enclosure 460. The emitter 468 may further comprise one or more filters capable of blocking unwanted portions and/or wavelengths of EO radiation. As a non-limiting example, a low-pressure mercury-vapor lamp emits EO radiation at peak wavelengths of approximately 184 nm and 254 nm. While both wavelengths can be used to sanitize a PD 180, EO radiation of 184 nm will also produce ozone, which may be undesirable. Accordingly, the low-pressure mercury-vapor lamp may be used in conjunction with a filter designed to block 184 nm EO radiation while allowing 254 nm EO radiation to pass through.

As disclosed above, the enclosure 460 may comprise an interior portion or region configured to receive the PD 180. An inner surface of the enclosure 460 may be configured to direct EO radiation to the PD 180. Accordingly, in some embodiments, portions of the interior surface of the enclosure 460 may comprise reflective material configured to reflect emitted EO radiation to the PD 180 such that the entire surface of the PD 180 is exposed thereto. In some embodiments, substantially all of the surface of the enclosure 460 is configured to reflect EO radiation. As used herein, the term "substantially" is given to mean that a property, shape, or configuration is not necessarily completely present but is sufficiently present to approximate performance as if the property, shape, or configuration were exactly as described. For example, if substantially all of a surface of the enclosure 460 is configured to reflect EO radiation, there may be no difference or only a minor difference in sanitation of the PD 180 within the enclosure 460 as compared to the case where the entire surface is configured to reflect EO radiation. Alternatively, only certain portions of the surface may be composed of reflective material (e.g., portions that face the PD 180). In embodiments where reflective material is used, the PD 180 may be exposed to reflected sanitizing EO radiation that reaches the PD 180 at oblique angles to minimize shadowing on the surface of the PD 180. The shadowing may be caused, for example, by particles on the surface of the PD 180; by features, such as seams or buttons, on the surface of the PD 180; or by scratches or other flaws in the surface of the PD 180. In yet another embodiment, no reflective material is used, but rather the emitters 468 of the controller 410 are arranged so that the entire surface of the PD 180 is directly exposed to EO radiation. In some embodiments, where the enclosure 460 is configured to receive a plurality of the PDs 180, the position the PDs 180 therein is such that the entire surface of each PD 180 is directly or indirectly exposed to the EO radiation.

In some embodiments, the sanitization station 150 may comprise a PD support 462 that is configured to maintain the PD 180 at a particular orientation and/or position within the enclosure 460. The PD support 462 may be configured to maintain the PD 180 in an orientation and/or position configured to allow EO radiation emitted by the emitter 468 to irradiate substantially the entire surface of the PD 180. In some embodiments, the PD support 462 may be transparent (or substantially transparent) to the EO radiation emitted by the emitter 468. Accordingly, the PD support 462 may be composed of EO transparent materials. The support member may be made of glass, plastic, polymer, ceramic, quartz, or other suitable materials sufficiently transparent to the EO radiation emitted by the controller 410. In some embodiments, the emitter 468 may be placed below the PD support 462 such that sanitizing EO radiation is emitted through the PD support 462 onto the surface of the PD 180. The intensity of the emitters 468 located below the PD support 462 may be increased relative to the other emitters 468 to compensate for partial absorption of the sanitizing EO radiation by the PD support 462. In some embodiments, the PD support 462 may be configured to filter EO radiation and/or otherwise modify EO radiation emitted by the emitter 468.

In some embodiments, the PD support 462 may comprise a flat support member (e.g., plate) configured to hold the PD 180 in a horizontal orientation. In some embodiments, a connector of the charger may be rigidly attached to the PD 180 such that the PD 180 is secured within the enclosure 460. Alternatively, or in addition, the PD support 462 may comprise a textured surface capable of preventing or minimizing movement of the PD 180. In some embodiments, the PD support 462 further comprises raised members that prevent the PD 180 from sliding off the PD support 462. The raised members may be transparent to the sanitizing EO radiation. In another embodiment, the raised members are reflective to the sanitizing EO radiation.

The HMI components 420 may comprise a hands-free HMI element 422, which may be configured to selectively open the enclosure 460 to receive a PD 180 and close the enclosure 460 in preparation for performing a sanitization operation in response to hands-free user inputs. As used herein, a "hands-free" input refers to an input that does not require the user to touch the sanitization station 150 and/or the HMI components 420 thereof. The hands-free HMI element 422 of the sanitization station 150 may include, but is not limited to: a motion sensor, a gesture sensor, an acoustic sensor, a camera, an image capture device, a capacitive sensor, a thermal sensor, and/or the like. The hands-free HMI element 422 may be configured to open the enclosure 460 to receive a PD 180 (by use of the actuator 470) in response to a first hands-free input and to perform a sanitization operation in response to a second hands-free input (e.g., close the enclosure 460 and/or activate the emitters 468, as disclosed herein).

In some embodiments, the enclosure 460 may comprise an acoustic conduit, which may comprise an opening and/or exit configured to provide an acoustic path or channel between the interior and exterior of the enclosure 460 (not shown in FIG. 4A to avoid obscuring the details of the illustrated embodiments). Sound emitted by the PD 180 within the enclosure 460 may pass through the acoustic conduit to the exterior of the enclosure 460. The acoustic conduit may, therefore, allow the user to hear alerts or alarms generated by the PD 180 while the PD 180 is within the enclosure 460. The acoustic conduit may be further configured to prevent EO radiation from escaping the enclosure 460. Accordingly, the acoustic conduit may be configured to block and/or prevent optical paths between the interior of the enclosure 460 and the exterior of the enclosure 460. In some embodiments, a shape of the acoustic conduit may be configured to block EO radiation; the acoustic conduit may be curved, tapered, and/or otherwise adapted to prevent EO radiation leakage. Alternatively, or in addition, an outer surface of the acoustic conduit may be composed of materials configured to absorb EO radiation emitted by the emitter 468. The acoustic conduit may be configured such that there is no line-of-sight or optical path from the interior of the enclosure 460 to the exterior of the enclosure 460. In some embodiments, the acoustic conduit comprises a narrow slot leading from the interior of the enclosure 460 to the exterior of the enclosure 460. In some embodiments the acoustic conduit comprises a membrane of EO radiation absorptive material configured to block EO radiation, while readily allowing acoustic signals to pass through. In some embodiments filaments of EO radiation absorptive material are placed within the acoustic conduit to absorb sanitizing EO radiation while allowing acoustic signals to pass.

In some embodiments, the enclosure 460 and/or acoustic conduit are configured to amplify sounds therein (e.g., amplify acoustic signals generated within the enclosure 460). In some embodiments the acoustic conduit comprises an acoustic megaphone configured to amplify sound or other acoustic signals originating within the enclosure 460. In some embodiments, the acoustic conduit comprises a horn configured to resonate acoustic signals.

In some embodiments, the sanitization station 150 comprises a charger configured to charge or recharge the PD 180 disposed therein (not shown in FIG. 4A to avoid obscuring the details of the illustrated embodiments). In at least one embodiment, the charger is configured to charge multiple PDs 180. The charger may comprise a connector configured to supply electrical power to the PD 180. In one embodiment, the charger includes a connector for each of a plurality of the PDs 180 that may be placed within the enclosure 460. The connector may be a physical connector that plugs into the PD 180, such as a Universal Serial Bus (USB) connector, mini-USB connector, micro-USB connector, 30-pin connector, proprietary connector, or the like. Alternatively, or in addition, the charger may comprise an inductive coil to transfer power wirelessly to the PD 180. In some embodiments the connector of the charger may be further configured to act as a docking connector for the PD 180 (e.g., communicate data between the PD 180 and a computing device, hub, or the like). The sanitization station 150 may be configured to act as an end node of the data connection or may be configured to act as an intermediary node (hub) used to establish a data connection between the PD and another external computing device. In some embodiments the charger may comprise a removable adaptor capable of connecting to various different types of connectors and/or PDs 180. In some embodiments the connector of the charger is extendable so that the PD 180 can be positioned at different locations and/or orientations within the enclosure 460.

In some embodiments the charger comprises a pass-through port configured to allow a cord or cable of a third-party charger to pass into the enclosure 460. The port and/or opening may be configured to prevent EO radiation from escaping the enclosure 460. Accordingly, the port and/or opening may comprise a gasket, pass-through cable, or other mechanisms and/or structures for blocking EO radiation. Alternatively, the charger may comprise an intermediary cable or cord with an exterior connector for connecting to a third-party charger and an interior connector.

As disclosed above, the controller 410 may be configured to control the charging and/or sanitizing operations of the sanitization station 150. The controller 410 may comprise one or more of: a circuit, a chip, a package, a microprocessor, a microcontroller, a central processing unit, a general-purpose processing unit, a special-purpose processing unit, processing circuitry, logic circuitry, an integrated circuit (IC), a System on a Chip (SoC), a Programmable System on a Chip (PsoC), a System in Package (SiP), an Application-specific Integrated Circuit (ASIC), configurable circuitry, programmable circuitry, a Field Programmable Gate Array (FPGA), a Complex Programmable Logic Device (CPLD), a Programmable Logic Array (PLA), and/or the like. In some embodiments the controller 410 comprises a timer module and/or process configured to track time information pertaining to the operation of the sanitization station 150. The controller 410 references the timing information to determine when to cause the controller 410 to stop emitting EO radiation. The controller 410 may, therefore, control the exposure time of the PD 180. In some embodiments, the controller 410 automatically deactivates the controller 410 after a predetermined irradiation time. In some embodiments, the exposure time may be determined from user input (received via the HMI components 420). In another embodiment, the exposure time is automatically calculated by the controller 410; the exposure time may be selected according to the intensity, wavelength, and/or type of EO radiation emitted by the controller 410. In some embodiments, the amount of exposure time may vary according to the contamination level of the PD 180.

As disclosed above, the controller 410 may be coupled to the detector 466 to determine whether the enclosure 460 is in a closed configuration. The controller 410 may be configured to deactivate the controller 410 while the enclosure 460 is not in the closed configuration. The controller 410 may be further configured to monitor the closure status of the enclosure 460 during operation of the controller 410 (by use of the detector 466), and may interrupt sanitizing operations in response to determining that the enclosure 460 is no longer in the closed configuration. In some embodiments, the controller 410 may be configured to continue a sanitizing cycle (e.g., reactivate the controller 410, but not reset a timer associated with the cycle) in response to closing the enclosure 460. In some embodiments, the sanitizing cycle may be configured to continue the sanitizing cycle if the enclosure 460 is closed within a time threshold; otherwise, the controller 410 may be configured to restart the sanitizing cycle.

In some embodiments the controller 410 is configured to automatically activate the controller 410 in response to detecting a PD 180 within the enclosure 460. In some embodiments the controller 410 determines that a PD 180 is present within the enclosure 460 by determining whether a PD 180 is connected to the charger. In some embodiments, the sanitization station 150 comprises one or more sensors configured to determine whether a PD 180 is present within the enclosure 460. Such sensors may include, but are not limited to, optical sensors, weight sensors, capacitive sensors, resistive sensors, pressure sensors, mechanical switches, or the like.

The controller 410 may be configured to periodically perform self-sanitization operations. Accordingly, in some embodiments, the controller 410 may be configured to automatically activate the controller 410 when the enclosure 460 is closed, regardless of whether the PD 180 is present within the enclosure 460. The self-sanitization cycle may ensure that the enclosure 460 is free from bacteria and/or other contaminants in areas obscured by the PD 180. In some embodiments, a self-sanitization process may be invoked manually through the HMI components 420.

The sanitization station 150 may further comprise one or more latching and/or securing mechanisms configured to maintain the enclosure 460 in a closed configuration. The mechanisms may be further configured to prevent EO radiation from escaping the enclosure 460. In some embodiments, the enclosure 460 may comprise a pair of magnets configured to secure two halves of the enclosure 460 to one another. In some embodiments, the enclosure 460 may comprise a spring in a hinge that applies a closing force thereto. In some embodiments, the enclosure 460 comprises a bi-stable spring, or other suitable mechanism, where one stable state corresponds to a closed configuration and the other stable state corresponds to an open position. In one embodiment, the enclosure 460 comprises a slide member, such as a slide member on a drawer or cover, that slopes toward a closed position such that a drawer or cover is drawn toward the closed position by gravity. In some embodiments the latching mechanism is integrated with the detector 466 for determining whether the enclosure 460 is in a closed configuration.

In some embodiments, the enclosure 460 may comprise an EO radiation seal configured to prevent leakage of EO radiation. The radiation seal may comprise a gasket and/or lips formed at the opening 464 of the enclosure 460. In some embodiments, the EO radiation seal(s) may comprise material configured to absorb EO radiation. Portions of the EO radiation seal(s) may be formed from reflective materials configured to reflect EO radiation back into the enclosure 460.

In some embodiments, the opening 464 of the sanitization station 150 comprises a front panel 465 having an inner surface 467. The front panel 465 may be coupled to a bottom portion of the enclosure 460 by a hinge 469 or other structure. The actuator 470 may be configured to reposition the front panel 465 to thereby open and close the enclosure 460. When in the closed configuration, the front panel 465 may be coupled to an outer surface of the enclosure 460 thereby enclosing an interior region of the enclosure 460. When in the open configuration, the front panel 465 may rotate away from the enclosure 460 (via bottom hinges 469) thereby exposing the interior of the enclosure 460. The inner surface 467 of the front panel 465 may be angled such that a PD 180 placed thereon remains secured on the front panel 465 as the front panel 465 moves from the open configuration (in which the front panel 465 is substantially horizontal) to the closed configuration (in which the front panel 465 is substantially vertical). The inner surface of the inner surface 467 may be angled such that, when in the open configuration, the end of the inner surface 467 closest to the hinge 469 (and the bottom of the enclosure 460) is raised relative to the opposite end of the inner surface 467.

The sanitization station 150 may further comprise a diagnostic module 478, which may be configured to perform diagnostic operations on the sanitization station 150. The diagnostic operations may comprise, inter alia, determining a status of one or more of the emitters 468 of the sanitization station 150 (e.g., determine an output level and/or remaining life of respective emitters 468). The diagnostic module 478 may comprise and/or be communicatively coupled to an object detector 480 and EO meter 490. The object detector 480 may be configured to detect object(s) within the interior 461 of the enclosure 460 (verify that the interior 461 is empty prior to performing diagnostic operations). The object detector 480 may comprise an optical object detector, a laser optical detector, and/or the like. The object detector 480 may comprise a laser generator and a laser detector. The laser generator may be configured to produce one or more laser outputs, and the detector may be configured to detect corresponding signals reflected and/or diffused within the interior 461. Alternatively, or in addition, the laser generator may direct laser signals through the interior 461 to one or more laser detectors within the enclosure 460 (such that the laser signals would be blocked by objects within the interior 461). The EO meter 490 may be configured to measure EO radiation emitted by respective emitters 468 within the enclosure 460.

In some embodiments, the diagnostic module 478 is configured to perform diagnostic operations, which comprise: a) verifying that the enclosure 460 is in a closed configuration, b) verifying that the enclosure 460 is empty (i.e., verifying that a PD 180 or other object is not within the enclosure 460, c) selectively activating respective emitters 468, and d) metering EO radiation output by the respective emitters 468. The diagnostic operations may further comprise comparing the metered outputs of the respective emitters 468 to one or more thresholds, and assessing a status, output efficiency, output level, remaining life, and/or other characteristics of the respective emitters 468 based on the comparing. The diagnostic operation may comprise determining that the output of one or more of the emitters 468 fails to satisfy a minimum threshold and, as such, must be replaced. The diagnostic module 478 may be configured to communicate diagnostic information pertaining to the sanitization station 150 to the sanitization manager 110 and/or HMI components 420.

Figure 4B:
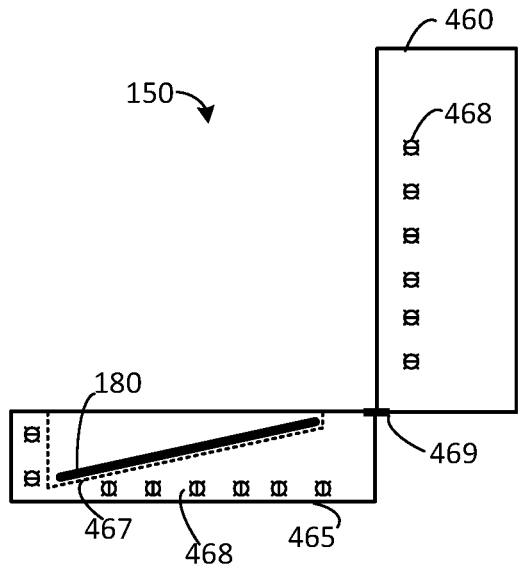
FIG. 4B depicts further embodiments of a sanitization station.
Figure 4C:
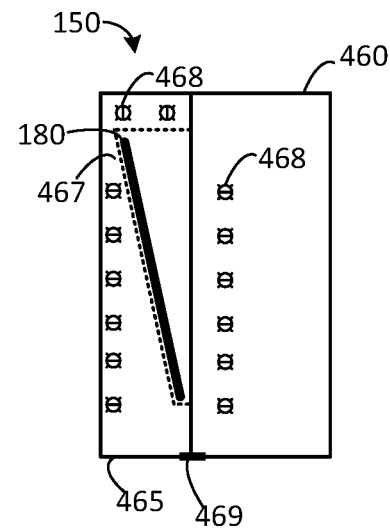
FIG. 4C depicts further embodiments of a sanitization station.

FIGS. 4B and 4C depict embodiments in which the front panel 465 rotates via the bottom hinges 469 (or other members) from an open configuration to a closed configuration (and vice versa). As illustrated in FIG. 4B, when in the open configuration, the inner surface 467 of the front panel 465 is exposed to receive a PD 180. The inner surface 467 may be angled such that an end proximate to the enclosure 460 is raised relative to the end farther from the enclosure 460. As illustrated in FIG. 4C, the actuator 470 may rotate the front panel 465 to the closed configuration (via the bottom hinges 469). In the closed configuration, the PD 180 may be secured within the enclosure 460 due to, inter alia, the angle of the inner surface 467 of the front panel 465. The PD 180 may be thereby secured within the enclosure 460 without the need for additional securing members, which may block and/or diffuse EO radiation of the emitters 468 (and prevent the PD 180 from being fully sanitized). The inner surface 467 may be formed of materials that are substantially transparent to the EO radiation emitted by the EO emitters 468. The front panel 465 and/or inner surface 467 may comprise one or more notches, grooves, and/or the like to further secure the PD 180 within the enclosure 460. As disclosed above, the actuator 470 may be configured to open and close the front panel 465 in response to hands-free inputs received via the HMI components 420 (via the hands-free HMI element 422). In such embodiments, a user 182 may sanitize a PD 180 without touching the exterior surface of the sanitization station 150. The user 182 may touch the inner surface 467 of the front panel 465 while placing the PD 180 therein (and removing the PD 180 after sanitation is complete). In some embodiments, the sanitization station 150 is configured to sanitize the inner surface 467 before opening the front panel 465 to ensure that the user 182 and/or PD 180 are not subject to any preexisting contaminants within the enclosure 460. Although FIGS. 4B and 4C illustrate particular embodiments for hands-free operation of a sanitization station 150, the disclosure is not limited in this regard and could be adapted to use any suitable hands-free mechanisms including, but not limited to: a self-actuated tray to slide into and out of the enclosure 460, an insertion slot, a rotating opening, and/or the like.

Referring back to FIG. 4A, the sanitization station 150 disclosed herein may comprise and/or be communicatively coupled to a sanitization station monitor 120C. The sanitization station monitor 120C may be configured to capture information pertaining to sanitization operations performed by the sanitization station 150 (e.g., obtain sanitization records, as disclosed herein). The sanitization station monitor 120C may be further configured to transmit the monitoring metadata 113 corresponding to the sanitization operations to the sanitization manager 110 via the network 102 (and by use of network interface components 440). The network interface components 440 may include, but are not limited to: network interface devices, network interface ports, network interface cards, wired network interface components, network interface ports, wireless network interface components (e.g., wireless network transmitters, receivers, transceivers, and/or the like), communication buses, communication drivers, and/or the like.

The sanitization station monitor 120C may comprise station interface components 430, which may be configured, inter alia, to determine the device identifier 181 of the PD 180 being sanitized within the enclosure 460 of the sanitization station 150. The station interface components 430 may be configured to capture the device identifiers 181 using any suitable techniques and/or devices, including, but not limited to: bar code scanners, bar code readers, Optical Character Recognition (OCR) systems, the network interface components 440 (e.g., a Bluetooth® network interface components, NFC network interface components, and/or the like), RFID readers, manual input devices, software interfaces (e.g., an interface to a management client 118 operating on the PD 180), bus interface components (e.g., Universal Serial Bus (UBS) interface components, USB-C interface components, Lightning® interface components, etc.), and/or the like. The station interface components 430 may be further configured to capture information pertaining to respective sanitization operations, which may include, but is not limited to: an identifier of the sanitization station 150, a location of the sanitization station 150, an identifier of the user 182 who performed the sanitization operation, a duration of the sanitization operation, a type of sanitization operation (e.g., quick, standard, deep, or the like), EO radiation used in the sanitization operation, an indication of whether the sanitization operation was fully completed, the time the sanitization operation was initiated, the time the sanitization operation was completed, diagnostics pertaining to the PD 180 and/or sanitization station 150, an authentication credential, a signature, and/or the like. The sanitization station monitor 120C may be further configured to transmit the monitoring metadata 113 pertaining to sanitization operations to the monitor 112 of the sanitization manager 110 via the network 102 (by use of the network interface components 440), as disclosed herein. Although, in the FIG. 4A embodiment, the sanitization station monitor 120C is embodied separately from the sanitization station 150, the disclosure is not limited in this regard. In other embodiments, the sanitization station monitor 120C may be embodied as components of the sanitization station 150 (e.g., as part of the same device).

Figure 4D:
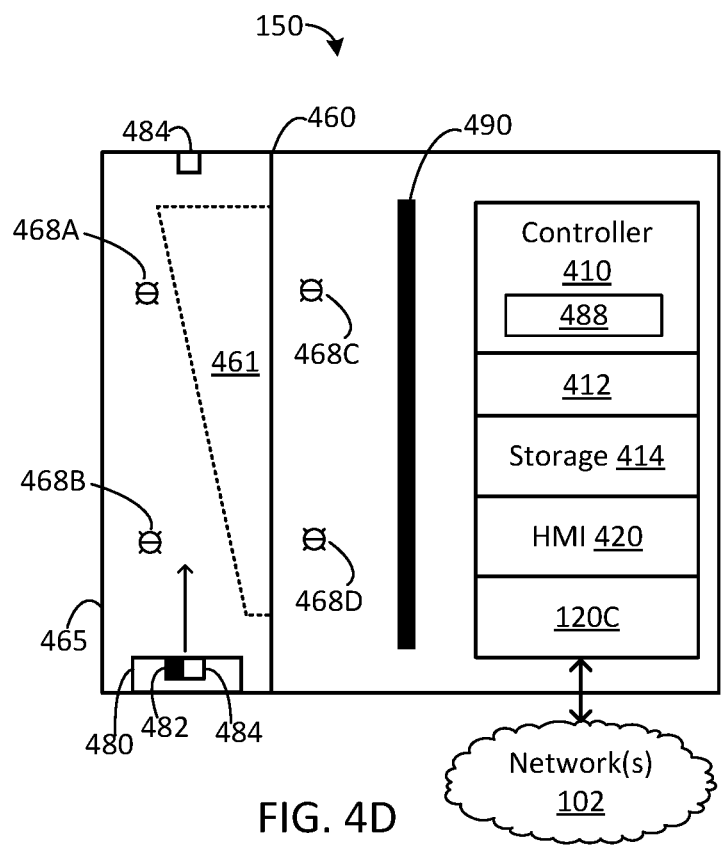
FIG. 4D depicts further embodiments of a sanitization station.

FIG. 4D is a simplified diagram illustrating another embodiment of a sanitization station 150. In the FIG. 4D embodiment, the diagnostic module 478 is embodied as a component of the controller 410. The diagnostic module 478 may be embodied as logic and/or circuitry elements of the controller 410, firmware, instructions recorded on a non-transitory storage medium (e.g., storage component 414), and/or the like. The diagnostic module 478 may be configured to perform diagnostic operations by use of an object detector 480 and one or more EO meters 490. As disclosed above, the object detector 480 may be configured to determine whether the interior 461 of the enclosure 460 is empty (whether a PD 180 or other object has been placed into the interior 461). The object detector 480 may comprise a signal transceiver, signal emitter, and/or signal receiver. In some embodiments, the object detector 480 comprises a signal generator (a laser) 482 configured to output an EO signal into the interior 461 of the enclosure 460. The object detector 480 may further comprise a signal detector 484 to detect return signal(s) corresponding to the generated EO radiation signals. The signal detector 484 may be configured to detect a signal reflected and/or diffused within the interior 461. Alternatively, or in addition, the signal detector 484 may be configured to detect an EO signal directed thereto (e.g., be disposed on an opposite end of the interior 461. The sanitization station 150 may further comprise one or more EO meters 490, which may be configured to measure EO radiation produced by respective emitters 468 within the interior 461 of the enclosure 460. The diagnostic module 478 may be configured to implement diagnostic operations, as disclosed herein, which may comprise: a) ensuring that the sanitization station 150 is in a closed configuration, b) verifying that the interior 461 of the enclosure 460 is empty (using the object detector 480), c) configuring respective emitters 468 to emit EO radiation, and d) measuring the EO radiation produced by the respective emitters 468 (by use of the EO meter 490). In the FIG. 4D embodiment, implementing a diagnostic operation may comprise selectively activating each of emitters 468A-D individually. The EO meter 490 may determine an amount of EO radiation produced by each respective EO emitter 468A-D. The EO meter 490 may be located within the interior 461 such that the EO meter 490 is in substantially similar proximity to each of the EO emitters 469A-D. Alternatively, or in addition, the sanitization station 150 may comprise a plurality of EO meters 490 in substantially the same proximity to respective EO emitters 468A-D. The diagnostic module 478 may be further configured to track EO outputs of the respective EO emitters 468A-D over time in order to, inter alia, detect deterioration thereof. The diagnostic information may be recorded in the storage component 414 and/or communicated to the sanitization manager 110 via the network 102. The diagnostic module 478 may compare the EO output of each EO emitter 468A-D to one or more thresholds in order to, inter alia, identify EO emitters 468A-D that need to be replaced. If the EO output of one or more of the emitters 468A-D is below a minimum threshold, the diagnostic module 478 make take the sanitization station 150 out of service until the EO emitters 468A-D are replaced. The diagnostic module 478 may provide diagnostic information to the sanitization manager 110, which may inform users 182 of outages through one or more of a PD 180, electronic monitoring device 1206, communication device 183, and/or the like.

Figure 5:
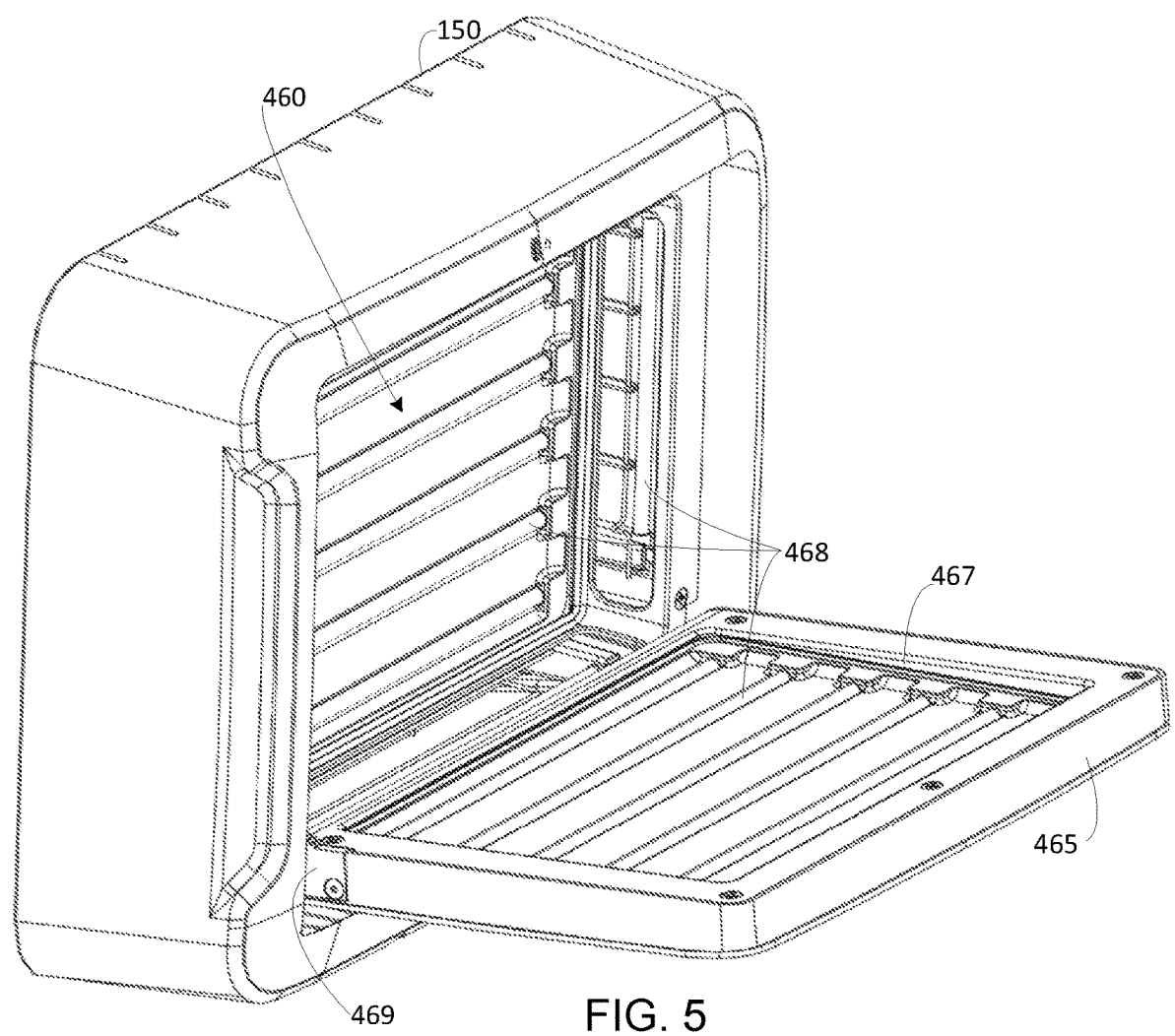
FIG. 5 depicts further embodiments of a sanitization station.

FIG. 5 depicts another embodiment of the sanitization station 150 disclosed herein. FIG. 5 depicts the sanitization station 150 in the open configuration in which the front panel 465 is rotated away from the enclosure 460 via the bottom hinges 469 (and the actuator 470, not shown to avoid obscuring the details of the illustrated embodiments). As illustrated, the inner surface 467 of the front panel 465 may be angled such that an end of the inner surface 467 proximate to the hinges 469 is raised relative to the opposite end. Accordingly, a PD 180 placed on the inner surface 467 may remain secured thereon when the sanitization station 150 transitions to the closed configuration (e.g., the front panel 465 rotates on the hinges 469 to cover the enclosure 460). The sanitization station 150 of the FIG. 5 embodiment may be configured to be mounted vertically (e.g., on a wall).

Referring back to FIG. 1, the sanitization manager 110 may comprise an interface 122, which may be configured to interface with PD 180, monitoring devices 120A-N, sanitization stations 150, and so on. The interface 122 may be embodied on the sanitization management server 111. The interface 122 may comprise a network communication interface (e.g., a web server), an application programming interface (API), and/or the like. Alternatively, or in addition, the interface 122 may be embodied by hardware components, such as HMI components 420 as disclosed herein (e.g., input devices, output devices, and so on).

Figure 6:
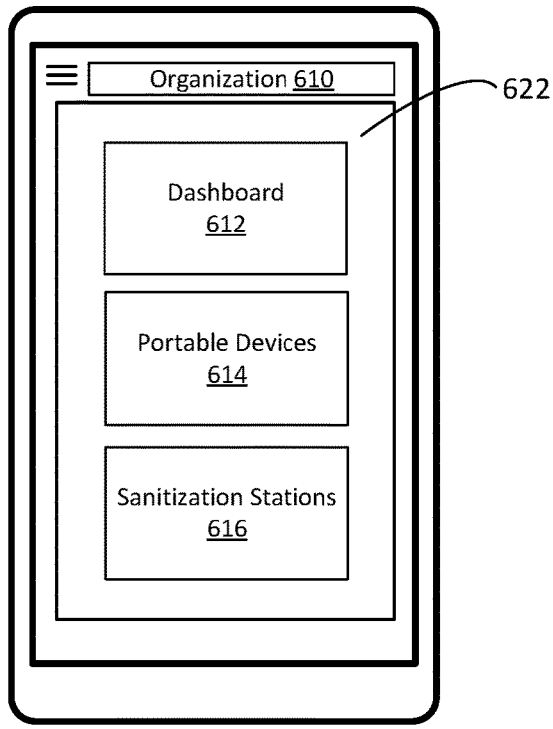
FIG. 6 depicts one embodiment of a management interface of a sanitization system.

FIG. 6 depicts one embodiment of an interface 622 for the sanitization management system 100 as disclosed herein. The interface 622 (and the other interfaces disclosed herein) may be embodied as one or more of: computer-readable code, electronic markup data, script data, and/or the like, which may be stored and/or recorded on a non-transitory storage medium. The interface 622 may be configured for display on a portable computing device (e.g., a PD 180, communication device 183, and/or the like). The interface 622 may identify an organization 610 associated with the sanitization management system 100. The interface 622 may comprise a dashboard component 612, which may be configured to provide information pertaining to the sanitization management system 100, such as the sanitization policy 119 being implemented by the sanitization manager 110, the status of monitoring devices 120A-N, information pertaining to the monitoring metadata 113 acquired by respective monitoring devices 120A-N (and corresponding sanitization management data 133), and so on. The interface 622 may include a portable devices component 614, which may be configured to manage the PDs 180 registered within the sanitization management system 100 (and/or corresponding monitoring devices 120A-N). The interface 622 may further include a sanitization stations component 616, which may be configured to manage the sanitization stations 150 of the sanitization management system 100.

Figure 7A:
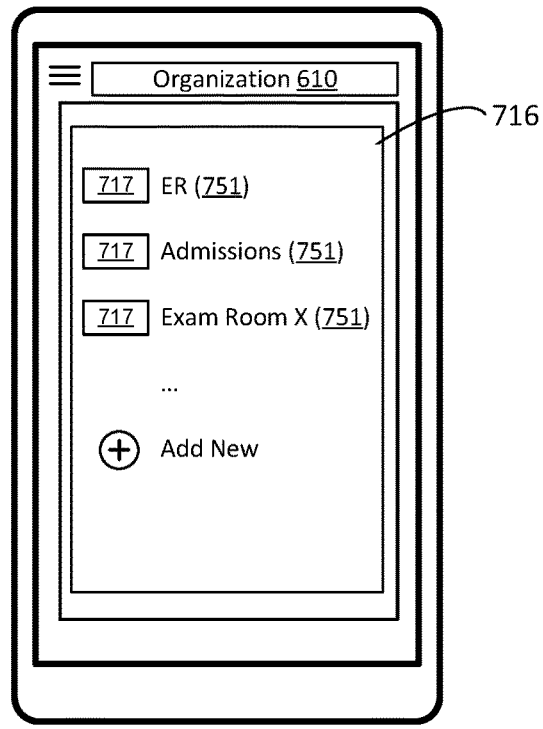
FIG. 7A depicts an embodiment of an interface for managing sanitization stations.

FIG. 7A depicts one embodiment of an interface 716 for managing sanitization stations 150 of the sanitization management system 100. The interface 716 may be accessed through the sanitization stations component 616 disclosed above. Alternatively, or in addition, the interface 716 may comprise a separate, independent interface provided by the sanitization manager 110.

The interface 716 may provide a listing of the sanitization stations 150 of the sanitization management system 100. The listing may include an entry for respective sanitization stations 150 registered in the sanitization management system 100. The interface 716 of the FIG. 7A embodiment shows three sanitization stations, which may be identified using respective label elements 751. The label elements may indicate the identifier 151 of the sanitization stations 150, a location of the sanitization stations 150, a name and/or label for the sanitization stations 150 (e.g., ER, Admissions, and Exam Room X), and/or the like. Each list element may further comprise a status indicator 717, indicating the current status of respective sanitization stations 150. The status indicator 717 may indicate one or more of: whether the sanitization manager 110 is in communication with the sanitization station 150 (through a communication network 102), whether the sanitization station 150 is operational, a configuration of the sanitization station 150, a maintenance status of the sanitization station 150 (e.g., number of hours since last service), and so on. The interface 716 may provide for configuring registered sanitization stations 150 (by selecting respective list elements of the sanitization stations 150) and/or registering new sanitization stations 150.

Figure 7B:
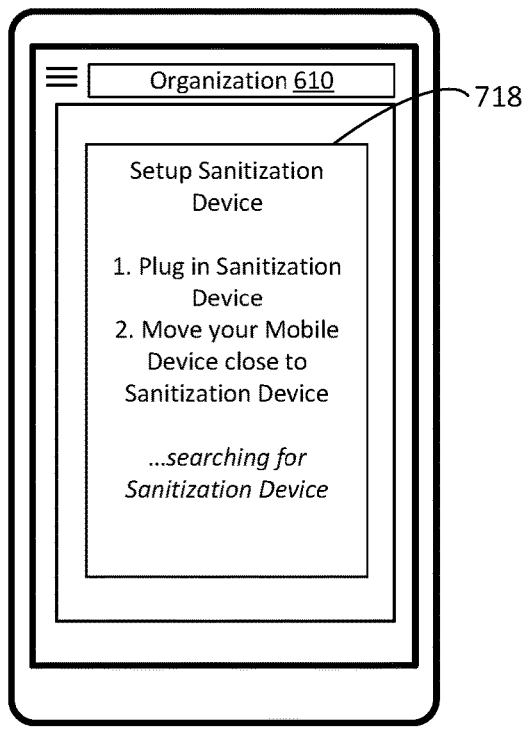
FIG. 7B depicts an embodiment of an interface for configuring a sanitization station.
Figure 7C:
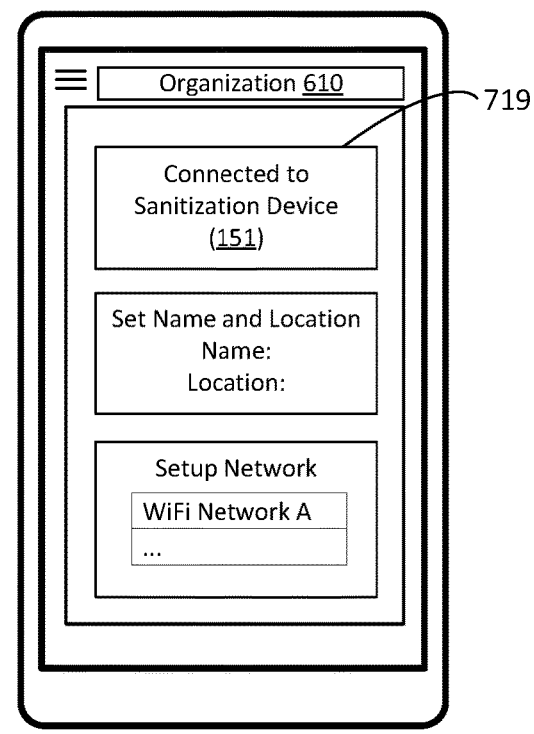
FIG. 7C depicts another embodiment of an interface for configuring a sanitization station.

FIG. 7B depicts one embodiment of an interface 718 for registering a sanitization station 150 with the sanitization management system 100. The interface 718 may be accessed through the interface components disclosed above. Alternatively, or in addition, the interface 718 may comprise a separate, independent interface implemented computing device (e.g., a PD 180, communication device 183, and/or the like), the sanitization manager 110, and/or the sanitization station 150 itself (by use of the HMI components 420, station interface components 430, and/or the like). As illustrated in FIG. 7B, the interface 718 may search for a sanitization station 150 in proximity to the computing device by use of: NFC, Bluetooth®, and/or other communication mechanism. FIG. 7C depicts an embodiment of an interface 719 for registering the sanitization station 150 after establishing communication therewith. The interface 719 may display an identifier 151 of the sanitization station 150. The interface 719 may comprise input components for specifying and/or editing the name and location of the sanitization. The interface 719 may comprise input components for setting up network communication for the sanitization station 150 (e.g., to enable the sanitization station 150 to communicate with the sanitization manager 110 via one or more communication networks 102). The information provided through the interface 719 (e.g., name, location, network configuration, and so on) may be stored persistently within the sanitization station 150, as disclosed herein (e.g., as persistent configuration and/or logging information 153).

Figure 7D:
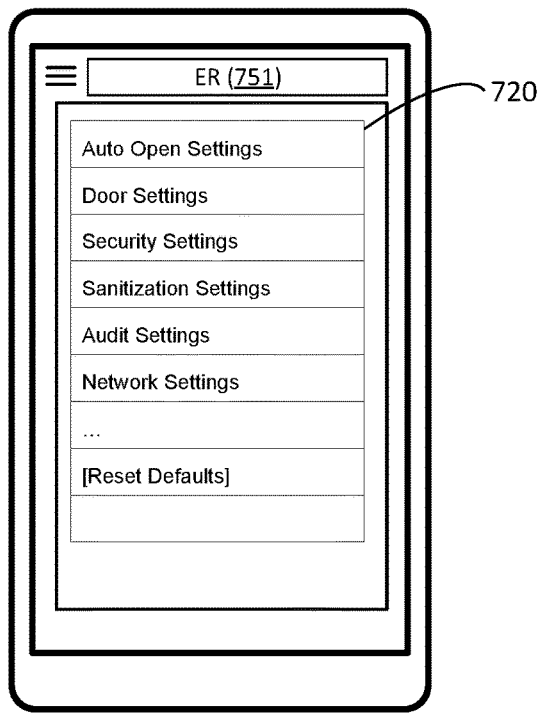
FIG. 7D depicts another embodiment of an interface for configuring a sanitization station.

FIG. 7D depicts an embodiment of an interface 720 for managing a sanitization station 150. The interface 718 may be accessed through the interface components disclosed above. Alternatively, or in addition, the interface 720 may comprise a separate, independent interface implemented computing device (e.g., a PD 180, communication device 183, and/or the like), the sanitization manager 110, and/or the sanitization station 150 itself (by use of the HMI components 420, station interface components 430, and/or the like). The interface 720 may identify the sanitization station 150 being configured (e.g., by use of a label element 751, as disclosed herein). The interface 720 may comprise components for configuring various aspects of the sanitization station 150, which may include, but are not limited to: components for configuring: auto open settings, door settings, security settings, sanitization settings, log settings, network settings, and so on. The interface 720 may further comprise a component for resetting the sanitization station 150 to a default configuration (and/or loading a predetermined configuration).

The door settings component may be used to specify whether to enable hands-free operation of the sanitization station 150 (e.g., whether the opening 464 of the enclosure 460 is configured to open automatically). The auto door settings component may provide for specifying events for triggering hands-free operation (e.g., in response to motion detection, voice activation, and/or the like). The auto door settings component may specify a speed at which the actuator 470 opens and/or closes the opening 464, an auto opening delay (a time between detecting a request to open the door from the time the actuator 470 begins moving the opening 464), and so on. A door settings component may configure open and/or closed settings for the sanitization station 150, such as an angle of the front panel 465 in the open configuration, an angle of the front panel 465 in the closed configuration, an amount of pressure and/or force to put on the front panel 465 during sanitization operations, and/or the like.

The security settings component may be used to configure security settings of the sanitization station 150, which may include, but are not limited to: whether authentication is required for use and/or manage the sanitization station 150, whether unregistered devices can be used within the sanitization station 150, and so on. The authentication required to use the sanitization station 150 may comprise any suitable credential (e.g., password, biometric, gesture, or the like). The security settings may specify that the sanitization station 150 cannot be used without an authentication credential. The authentication credential may be communicated to the sanitization station 150 through the HMI components 420 thereof, through the detector 466, through the station interface components 430, and/or the like. In some embodiments, the authentication credential may be provided by the management client 118, electronic monitoring device 1206, communication device 183, or the like (e.g., RFID tag). The sanitization station 150 may be configured to validate the authentication credential (and/or transmit the authentication credential to the sanitization manager 110 for verification). The sanitization station 150 may open the enclosure 460 so that a sanitization operation can be performed (and/or allow access to management interface(s) of the sanitization station 150) in response to verifying the authentication credential.

The audit settings component may be used to configure logging and/or audit functionality of the sanitization station 150 (e.g., whether logging is enabled, information to log, security and/or authentication protection for audit information, and so on). The network settings component may be used to configure network settings of the sanitization station 150, as disclosed herein.

Figure 8A:
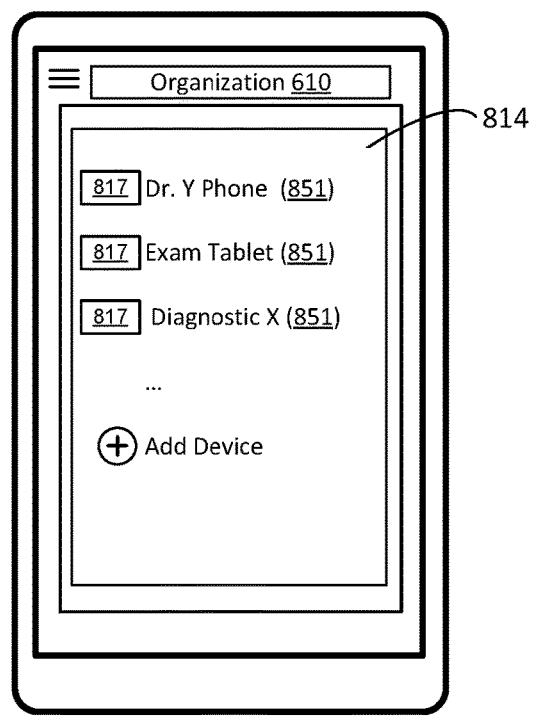
FIG. 8A depicts an embodiment of an interface for managing portable devices in a sanitization system.

FIG. 8A depicts an embodiment of an interface 814 for registering a PD 180 within the sanitization management system 100. The interface 716 may be accessed through the sanitization stations component 616 disclosed above. Alternatively, or in addition, the interface 716 may comprise a separate, independent interface provided by the sanitization manager 110.

The interface 814 may provide a listing comprising list entries for respective registered PD 180. The interface 814 of the FIG. 8A embodiment includes three list elements, each including a respective status indicator 817 and label 851 elements. The label 851 elements may provide information about the PD 180 and/or electronic monitoring device 120C (e.g., a label such as "Dr. Y Phone," "Exam Tablet," and "Diagnostic X"). The status indicator 817 elements may provide status information pertaining to respective PDs 180, which may include, but is not limited to: whether the PDs 180 are in compliance with the sanitization policy 119, whether the PDs 180 are in network communication with the sanitization manager 110, and so on.

Figure 8B:
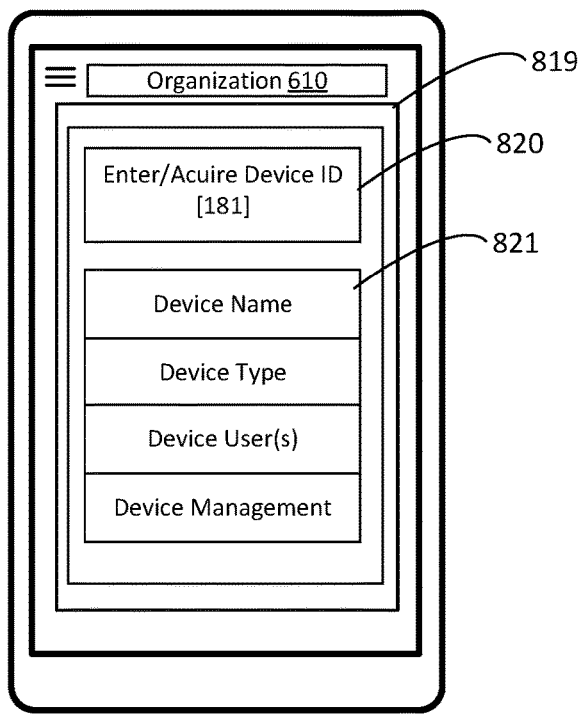
FIG. 8B depicts an embodiment of an interface for registering a portable device for sanitization management.

FIG. 8B depicts an embodiment of an interface 819 for registering a PD 180 with the sanitization management system 100. The interface 819 may be provided by the sanitization management server 111, management client 118, electronic monitoring device 120B, and/or the like. The interface 819 may identify the organization 610 associated with the sanitization management system 100 and/or specify the user of the PD 180 within the specified organization 610 (e.g., use name, role, group, and/or the like). The interface 819 may further comprise interface components 820 for specifying information pertaining to the PD 180, such as the device identifier 181, name, type, user(s), managers, and so on. The interface components 820 may be configured to acquire the device identifier 181 by one or more of: scanning an RFID tag on the PD 180, reading the PD 180, generating a device identifier 181, and/or the like. The information entered into the interface 819 may be transmitted to the sanitization manager 110 and/or stored as a PD record and/or PD state 117, as disclosed herein. In response, the sanitization manager 110 may manage sanitization of the PD 180, as disclosed here (e.g., by scheduling sanitization operations for the PD 180 in accordance with the sanitization policy 119).

Figure 9:
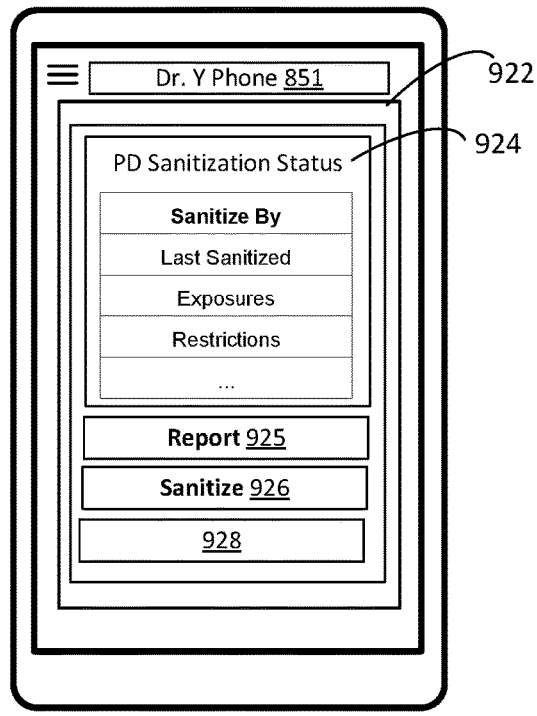
FIG. 9 depicts an embodiment of an interface for a portable device managed within a sanitization system.

FIG. 9 depicts an embodiment of an interface 922 pertaining to a PD 180 managed by the sanitization management system 100. The interface 819 may be provided by the sanitization management server 111, management client 118, electronic monitoring device 120B, and/or the like. The interface 922 includes a label 851 element identifying the PD 180 to which the interface 922 pertains. The interface 922 may be displayed on the PD 180 itself (e.g., on the "Dr. Y Phone" PD 180) and/or on a separate computing device. The interface 922 may include a PD sanitization status component 924 configured to display information pertaining to the current sanitization status of the PD 180 (e.g., PD state 117 and/or sanitization state 386, as disclosed herein), which may include, but is not limited to: a next sanitization time scheduled for the PD 180, an indication of the LST of the PD 180, potential exposures since the LST, restrictions on the PD 180, and so on.

The interface 922 may further comprise a reporting component 925, which may be configured to provide updated information pertaining to the current sanitization status of the PD 180. The reporting component 925 may provide for reporting potential contamination of the PD 180. The reporting component 925 may be used to report potential contamination of the PD 180 itself (e.g., when the interface 922 is operating on the PD 180 and/or electronic monitoring device 120B) and/or to report potential contamination of another PD 180. The reporting component 925 may provide for requiring the PD 180 to be sanitized immediately (e.g., designate a particular sanitization priority for the PD 180) and/or impose restrictions on the PD 180, as disclosed herein.

The interface 922 may further include a sanitization component 926, which may be configured to facilitate sanitization of the PD 180. The sanitization component 926 may indicate the location of nearby sanitization stations 150 and/or activate a sanitization station 150 (e.g., authenticate to a sanitization station 150, activate hands-free mode to open the enclosure 460, and/or the like).

A sanitization policy component 928 of the interface 922 may be configured to provide information pertaining to the sanitization policy 119 for the PD 180 and/or display audit records 115 pertaining to the PD 180. The sanitization policy component 928 may be further configured to create and/or modify the sanitization policy 119 for the PD 180 (based on whether a user of the interface 922 is authorized to create and/or edit sanitization policy 119 in the sanitization management system 100).

Figure 10:
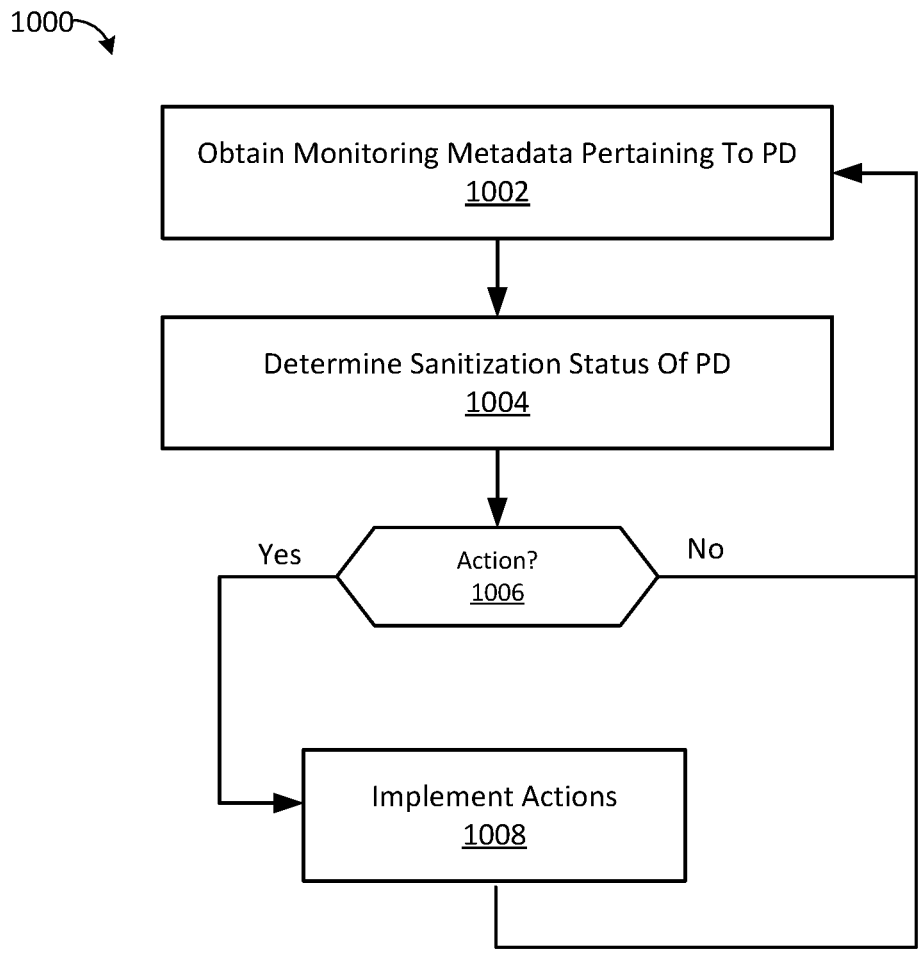
FIG. 10 is a flow diagram of one embodiment of a method for managing device sanitization.

FIG. 10 is a flow diagram of one embodiment of a method for managing device sanitization as disclosed herein. Portions of the steps, operations, and/or processes disclosed in connection with FIG. 10 (and the other flow diagrams herein) may be implemented using hardware components (e.g., computing devices, monitoring devices 120A-N, PD 180, and/or the like). Alternatively, or in addition, portions of the disclosed steps, operations, and/or processes may be embodied as computer-readable instructions stored on a non-transitory storage medium.

Step 1002 may comprise obtaining monitoring metadata pertaining to a PD 180. Step 1002 may comprise determining the LST of the PD 180, as disclosed herein (e.g., from a sanitization station 150). Step 1002 may further comprise determining that a sanitization operation was performed on the PD 180 (from a sanitization station 150 and/or sanitization station monitor 120C). Step 1010 may further comprise obtaining other monitoring metadata 113 from one or more monitoring devices 120A-N and/or deriving additional monitoring metadata 113 pertaining to the PD 180, as disclosed herein. Step 1002 may further comprise recording audit records 115 pertaining to the monitoring metadata 113 (e.g., audit records 115 corresponding to sanitization operations performed on the PD 180, potential contamination of the PD 180, and so on).

Step 1004 may comprise determining a sanitization status of the PD 180 based on the monitoring metadata 113 obtained at step 1004. Step 1004 may comprise comparing a time elapsed since the LST of the PD 180 to a one or more of a recommended sanitization period and/or maximum sanitization period for the PD 180. In some embodiments, step 1004 may comprise evaluating a sanitization policy 119 for the PD 180 (based on the obtained monitoring metadata 113). Step 1004 may further comprise detecting potential contamination of the PD 180 based on the monitoring metadata 113, as disclosed herein (e.g., based on the location(s), task(s), patient(s), of the PD 180 since the LST). Step 1004 may further include applying one or more rules defined in the sanitization policy 119, such as a time since LST rule, exposure rules, restriction rules, management action rules, and/or the like, as disclosed herein. Step 1004 may comprise determining and/or updating a PD state 117 for the PD 180. Step 1004 may comprise determining the sanitization state 386 of the PD 180, which may comprise one or more of: a next sanitization time, a sanitization priority, potential exposures of the PD 180 since the LST, restrictions on the PD 180, and so on, as disclosed herein.

Step 1006 may comprise determining whether to implement one or more management actions pertaining to the sanitization state of the PD 180. Step 1006 may comprise one or more of: determining whether to issue a notification and/or reminder indicating the time remaining until a sanitization operation must be performed on the PD 180 (in order to remain in compliance with the sanitization policy 119). Step 1006 may further comprise determining whether to issue a notification and/or reminder indicating that the PD 180 is due for sanitization. In some embodiments, step 1008 may comprise determining whether the PD 180 is out of compliance with the sanitization policy 119 (based on the determined sanitization state 386 of the PD 180). If the determining of step 1006 indicates that one or more management actions should be taken, the flow continues to step 1008; otherwise, the flow may continue back to step 1002.

Step 1008 may comprise implementing one or more management actions pertaining to the sanitization state of the PD 180, as disclosed herein. Step 1008 may comprise issuing a message, directive, command, and/or imperative pertaining to sanitization of the PD 180. Step 1008 may comprise sending a message to the user 182 of the PD 180 (e.g., as a text message or email sent to a communication device 183 of the user 182). Alternatively, or in addition, step 1008 may comprise issuing a message, directive, command, and/or imperative to the PD 180, one or more monitoring devices 120A-N, management personnel, administrative personnel, maintenance personnel, compliance personnel, and/or the like. Step 1008 may comprise sending computer-readable instructions to the PD 180 configured to cause the PD 180 to display a reminder notification. Alternatively, or in addition, step 1008 may comprise sending computer-readable instructions to cause the PD 180 to block and/or inhibit further operation until a sanitization operation is performed. Step 1008 may further comprise implementing one or more restrictions, as disclosed herein. Upon implementing the management actions, the flow may continue back to step 1002.

Figure 11:
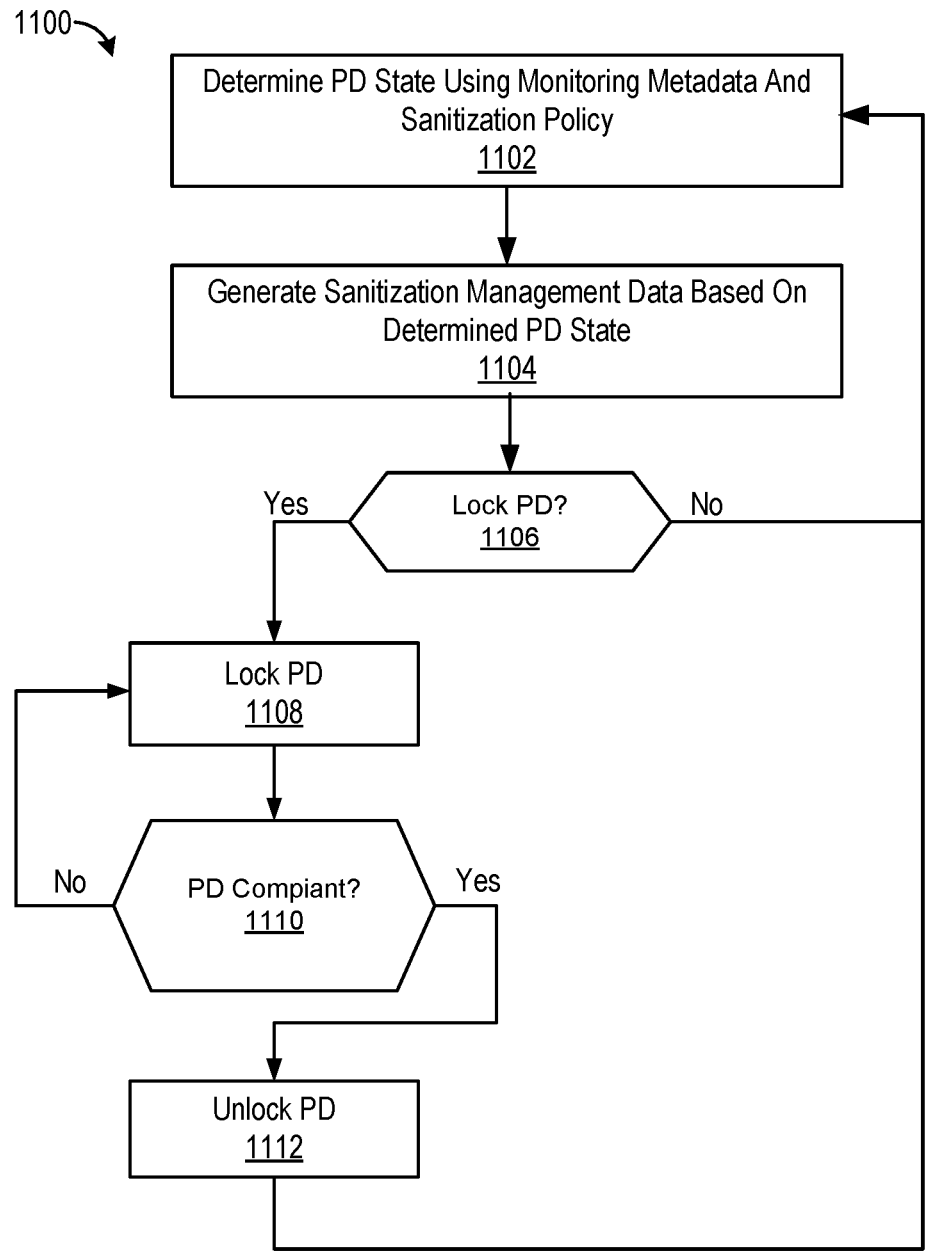
FIG. 11 is a flow diagram of another embodiment of a method for managing device sanitization.

FIG. 11 is a flow diagram of another embodiment of a method 1100 for managing device sanitization. Step 1102 may comprise determining the PD state 117 of a PD 180 in response to receiving monitoring metadata 113 from one or more monitoring devices 120A-N. Step 1102 may further comprise determining the sanitization state 386 of the PD 180 by, inter alia, applying rules of a sanitization policy 119 to the monitoring metadata 113, as disclosed herein.

Step 1104 may comprise generating sanitization management data 133 for the PD 180 based on the determined PD state 117 (and/or sanitization state 386). The sanitization management data 133 may comprise a next sanitization time for the PD 180, a sanitization priority, potential contamination of the PD 180, restrictions to apply to the PD 180, and so on, as disclosed herein. Step 1104 may comprise sending the sanitization management data 133 to one or more of: the PD 180, user(s) 182 of the PD 180, one or more communication devices 183, monitoring devices 120A-N (e.g., an electronic monitoring device 120C of the PD 180, and/or monitoring devices 120A-N for enforcing restrictions on the PD 180), other personnel, and/or the like.

Step 1106 may comprise determining whether to lock the PD 180. The determination of step 1106 may be based on the current sanitization state 386 of the PD 180 (e.g., priority of the sanitization operation, potential contamination of the PD 180, and/or the like), as disclosed herein. If the determination of step 1106 is to lock the PD 180, the flow continues to step 1108; otherwise, the flow proceeds to step 1102.

Step 1108 may comprise locking the PD 180, as disclosed herein (e.g., by sending computer-readable code and/or configuration information to the PD 180 and/or electronic monitoring device 120B).

Step 1110 may comprise determining whether the PD 180 is in compliance with the sanitization policy 119. Step 1110 may comprise determining whether a required sanitization operation has been performed on the PD 180 (based on monitoring metadata 113 from a sanitization station monitor 120C). If the determining of step 1110 is that the PD 180 is not compliant with the sanitization policy 119, the PD 180 may remain locked at step 1108; otherwise, the flow may continue to step 1112.

Step 1112 may comprise unlocking the PD 180, as disclosed herein (e.g., by sending computer-readable code and/or configuration information to the PD 180 and/or electronic monitoring device 120B). The flow may then proceed to step 1102.

Figure 12:
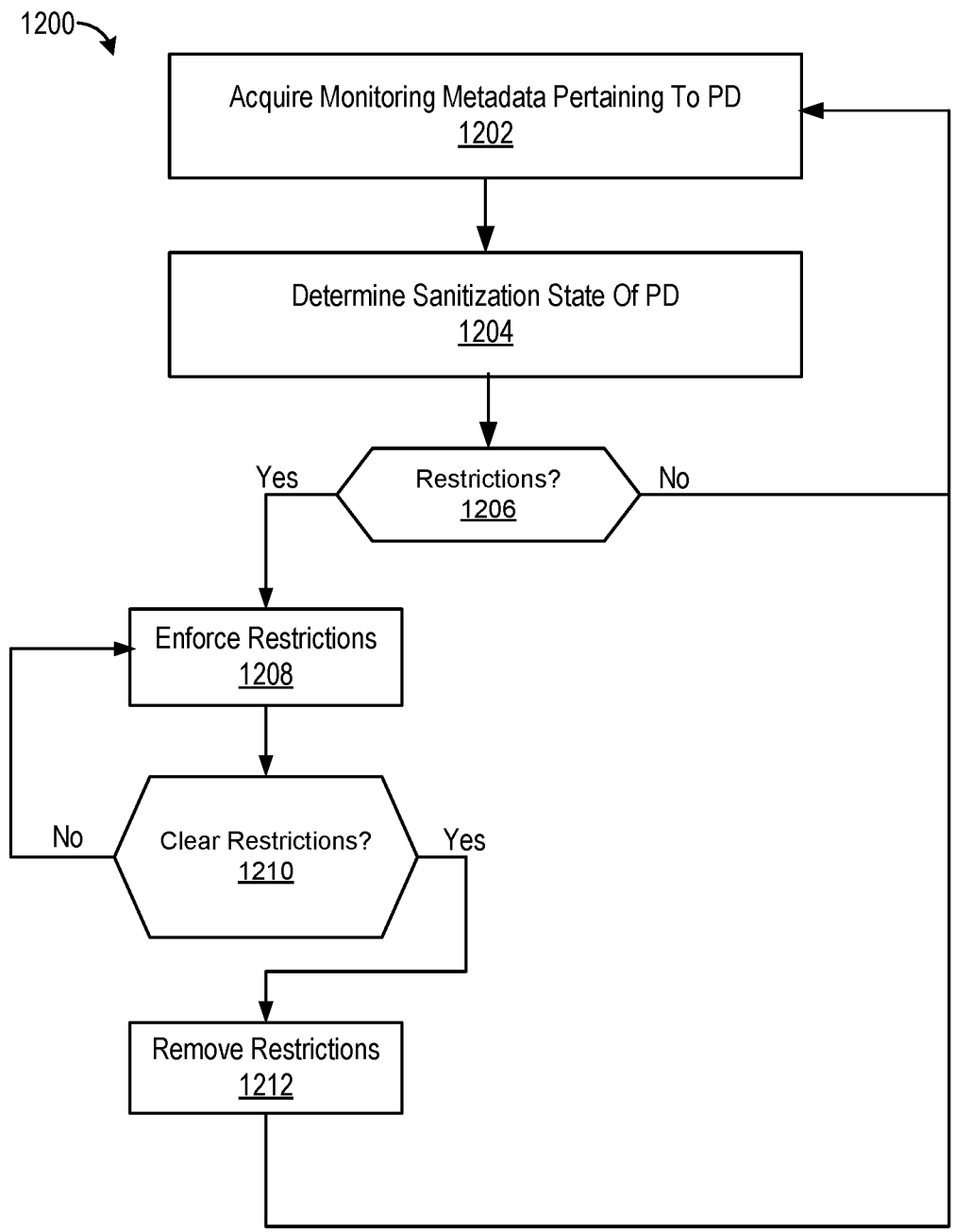
FIG. 12 is a flow diagram of another embodiment of a method for managing device sanitization.

FIG. 12 is a flow diagram of another embodiment of a method for managing device sanitization. Step 1202 may comprise acquiring monitoring metadata 113 pertaining to a PD 180, and step 1204 may comprise determining the sanitization state 386 of the PD 180 in response to the acquired monitoring metadata 113, as disclosed herein.

Step 1206 may comprise determining whether to impose restrictions on the PD 180. The determination of step 1206 may be based on rules defined by the sanitization policy 119 for the PD 180, which may include, but are not limited to: a time since LST rule, exposure rules, restriction rules, management action rules, and/or the like, as disclosed herein. If the determination of step 1206 is to impose one or more restrictions, the flow may continue to step 1208; otherwise, the flow may continue to step 1202.

Step 1208 may comprise enforcing one or more restrictions on the PD 180, as disclosed herein. Step 1208 may comprise transmitting sanitization management data 133 to the PD 180 and/or electronic monitoring device 120C, which may be configured to enforce the restrictions on the PD 180. The sanitization management data 133 may configure a management client 118 and/or electronic monitoring device 120C of the PD 180 to enforce one or more of a task restriction, a location restriction, a patient restriction, a patient condition restriction, and/or the like. The sanitization management data 133 may configure the PD 180 and/or electronic monitoring device 120C to prevent the PD 180 from being used for restricted tasks, taken into restricted locations, used with restricted patients and/or patient conditions, and/or the like. As disclosed herein, implementing the restrictions may comprise selectively locking the PD 180, asserting alarm notifications, and/or the like.

Step 1210 may comprise determining whether the restrictions can be cleared from the PD 180. Step 1210 may comprise determining whether a sanitization operation was performed on the PD 180 after the restrictions were imposed on the PD 180 (e.g., subsequent to performing steps 1202-1206). Step 1210 may comprise receiving additional monitoring metadata 113 pertaining to the PD 180 (e.g., receiving a sanitization record from a sanitization station monitor 120C indicating that the PD 180 has been sanitized). If the determination of step 1210 is that the restrictions can be cleared from the PD 180, the flow may continue to step 1212; otherwise, the flow may continue at 1208 (where the restrictions may remain in place).

Step 1212 may comprise removing the restrictions from the PD 180. Step 1212 may comprise updating the PD state 117 and/or sanitization state 386 of the PD 180 to indicate that the PD 180 is not subject to the restrictions of steps 1204-1208. Step 1212 may comprise transmitting sanitization management data 133 to one or more of the PD 180 and/or electronic monitoring device 120C configured to clear the restrictions from the PD 180.

In the disclosure, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with OCR systems, server computers, and/or communications networks have not been shown or described in detail to avoid unnecessarily obscuring descriptions of the embodiments.

Unless the context requires otherwise, as used herein, the word "comprise" and variations thereof, such as "comprises" and "comprising," are to be construed in an open, inclusive sense, that is as "including, but not limited to."

As used herein, "one embodiment" or "an embodiment" means that a particular feature, structure, or characteristic described in connection with the embodiment is included in at least one embodiment. Thus, the appearances of the phrases "in one embodiment" or "in an embodiment" herein are not necessarily all referring to the same embodiment. Furthermore, the particular features, structures, or characteristics may be combined or assembled in any suitable manner in one or more embodiments.

As used herein, the singular forms "a," "an," and "the" include plural referents unless the content clearly dictates otherwise. It should also be noted that the term "or" is generally employed in its broadest sense, that is, as meaning "and/or" unless the content clearly dictates otherwise.

The headings and Abstract of the Disclosure provided herein are for convenience only and do not interpret the scope or meaning of the embodiments.

Changes may be made to the details of the above-described embodiments without departing from the underlying principles of the invention. The scope of the present invention should, therefore, be determined only by the following claims.

The invention claimed is:

1. An apparatus, comprising:
an enclosure comprising an interior compartment configured to receive a portable device; and
a front panel of the enclosure configured to transition between an open position configured to provide access to the interior compartment and a closed position configured to enclose the interior compartment, the front panel comprising:
an inner surface configured to form an angled depression within the front panel such that a first end of the inner surface is disposed further within the front panel than a second end of the inner surface, the inner surface configured to hold the portable device within the angled depression such that the portable device is held at an angle relative to an axis of the front panel as the front panel transitions from the open position to the closed position, and
a first emitter disposed within the front panel of the enclosure, the first emitter configured to emit sanitizing electro-optical (EO) radiation into the interior compartment through the inner surface of the front panel.

2. The apparatus of claim 1, further comprising a second emitter configured to emit sanitizing EO optical radiation into the interior compartment, the second emitter disposed on a back wall of the enclosure that faces the inner surface of the front panel when the front panel is in the closed configuration.

3. The apparatus of claim 1, wherein the inner surface of the front panel forms the angled depression by being angled from a bottom portion at the first end to an upper portion at the second end, and wherein the angled depression is configured to secure the portable device at a vertical orientation that is offset from a vertical axis of the front panel when the front panel is in the closed position.

4. The apparatus of claim 3, wherein the bottom portion of the inner surface of the front panel comprises a notch configured to support the portable device in the vertical orientation when the front panel is in the closed position.

5. The apparatus of claim 1, wherein the front panel further comprises a series of grooves configured to stabilize the portable device.

6. The apparatus of claim 1, wherein the inner surface is configured to stabilize the portable device.

7. The apparatus of claim 1, further comprising a hinge configured to couple the front panel to a bottom wall of the enclosure.

8. The apparatus of claim 1, further comprising:
a controller configured to implement a sanitization operation on the portable device in response to the front panel transitioning to the closed position;
a detector configured to acquire an identifier of the portable device; and
a communication interface configured to transmit information pertaining to the sanitization operation on an electronic communication network, the information comprising the identifier of the portable device.

9. A sanitization device, comprising:
an enclosure comprising an interior compartment and front panel having a closed configuration adapted to enclose the interior compartment and an open configuration adapted to provide access to the interior compartment;
a first emitter disposed within the front panel of the enclosure, the first emitter configured to emit first sanitizing radiation into the interior compartment when the front panel is in the closed configuration;
a support member of the front panel, the support member configured to receive a portable device when the front panel is in the open configuration and to maintain the portable device within the interior compartment when the front panel is in the closed configuration, wherein the support member is substantially transparent to the first sanitizing radiation, wherein the support member is configured to form an angled depression within the front panel such that a first end of the support member is disposed further within the front panel than a second end of the support member, and wherein the portable device is held within the angled depression formed by the support member such that the portable device is held at an angle relative to an axis of the panel; and
an actuator configured to transition the front panel between the open configuration and the closed configuration in response to inputs received through a touchless input interface.

10. The apparatus of claim 9, wherein the touchless input interface comprises a sensor configured to detect movement in an area proximate to the enclosure, wherein the actuator is configured to transition the front panel from the closed configuration to the open configuration in response to the sensor detecting a first movement.

11. The apparatus of claim 9, wherein an interior surface of the enclosure is configured to reflect the first sanitizing radiation within the interior compartment.

12. The apparatus of claim 9, further comprising a second emitter disposed on a back wall of the enclosure, the second emitter configured to emit second sanitizing radiation into the interior compartment.

13. The apparatus of claim 9, wherein the support member is configured to secure the portable device at a first vertical angle when the front panel is in the closed configuration, the first vertical angle offset from a vertical axis of the front panel when the front panel is in the closed configuration.

14. The apparatus of claim 13, further comprising a hinge configured to couple a bottom end of the front panel to a bottom wall of the enclosure, wherein transitioning between the open configuration and the closed configuration comprises the actuator rotating the front panel about a fixed axis of rotation of the hinge.

15. The apparatus of claim 14, wherein the support member comprises a notch disposed at the bottom end of the front panel, the notch configured to support the portable device at the first vertical angle when the front panel is in the closed configuration.

16. An apparatus, comprising:
a panel having an open configuration and a closed configuration adapted to enclose an interior compartment of an enclosure;
a support plate configured to form an angled depression within the panel such that a first end of the support plate is disposed further within the panel than a second end of the support plate, wherein the support plate is further configured to:
receive a portable device within the angled depression when the panel is in the open configuration,
maintain the portable device within the angled depression as the panel transitions to the closed configuration, and
hold the portable device within the interior compartment of the enclosure while the panel is in the closed configuration, the portable device held within the angled depression formed by the support plate such that the portable device is held at an angle relative to an axis of the panel; and
one or more emitters capable of emitting sanitizing electro-optical radiation into the interior compartment of the enclosure.

17. The apparatus of claim 16, further comprising an attachment member configured to couple the panel to a wall of the enclosure and to provide for transitioning the panel between the open configuration and the closed configuration.

18. The apparatus of claim 17, wherein the attachment member comprises a hinge configured to rotate the panel from a horizontal position to a vertical position, the horizontal position corresponding to the open configuration and the vertical position corresponding to the closed configuration.

19. The apparatus of claim 18, further comprising a notch disposed at the second end of the support plate, the notch configured to support the portable device held within the angled depression as the panel rotates from the horizontal position to the vertical position.

20. The apparatus of claim 16, further comprising:
a touchless input interface; and
an actuator configured to transition the panel between the closed configuration and the open configuration in response to inputs received through the touchless input interface.

21. The apparatus of claim 16, wherein the one or more emitters comprise a first emitter disposed within the panel, the first emitter configured to transmit sanitizing electro optical radiation into the interior compartment of the enclosure.

22. The apparatus of claim 21, wherein the one or more emitters further comprise a second emitter disposed on a back wall of the enclosure, the back wall configured to face the support plate when the panel is in the closed configuration.

23. The apparatus of claim 16, further comprising:
- a controller configured to implement a sanitization operation on the portable device, the sanitization operation comprising configuring the one or more emitters to emit sanitizing electro-optical radiation into the interior compartment for a determined time period during which the panel is in the closed configuration and the portable device is held within the angled depression of the support plate;
- a detector configured to determine an identifier of the portable device; and
- a sanitization monitor configured to transmit a network communication message in response to completion of the sanitization operation, the network communication message comprising the determined identifier of the portable device.

* * * * *